(12) United States Patent
Konishi et al.

(10) Patent No.: US 6,706,932 B1
(45) Date of Patent: Mar. 16, 2004

(54) PROCESS FOR THE PREPARATION OF DIOL MIXTURES

(75) Inventors: Mitsuo Konishi, Okayama (JP); Koshiro Yokota, Kurashiki (JP); Eizaburou Ueno, Kurashiki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/129,143

(22) PCT Filed: Nov. 2, 2000

(86) PCT No.: PCT/JP00/07757

§ 371 (c)(1),
(2), (4) Date: May 2, 2002

(87) PCT Pub. No.: WO01/34543

PCT Pub. Date: May 17, 2001

(30) Foreign Application Priority Data

Nov. 5, 1999 (JP) ............................................ 11-315906
Jan. 24, 2000 (JP) ........................................ 2000-014402
Apr. 28, 2000 (JP) ........................................ 2000-129857

(51) Int. Cl.$^7$ ........................ C07C 27/00; C07C 27/04; C07C 31/18; C07C 29/00
(52) U.S. Cl. ........................................ 568/864; 568/861
(58) Field of Search ................................. 568/864, 861

(56) References Cited

U.S. PATENT DOCUMENTS 5,587,511 A * 12/1996 Salzburg et al. ............ 562/513
5,969,194 A * 10/1999 Hara et al. ................... 568/700

FOREIGN PATENT DOCUMENTS

| EP | 0712830 A1 | 5/1996 |
|----|-----------|--------|
| JP | 912492 A | 1/1997 |
| JP | 9132541 A | 5/1997 |
| JP | 1015388 A | 1/1998 |

* cited by examiner

*Primary Examiner*—Johann Richter
*Assistant Examiner*—Eluis O. Price
(74) *Attorney, Agent, or Firm*—Birch, Stewart, Kolasch & Birch, LLP

(57) ABSTRACT

Disclosed is a method for producing a diol mixture comprising 1,4-butanediol, 1,5-pentanediol and 1,6-hexanediol, which comprises: (A) providing a dicarboxylic acid mixture comprising succinic acid, glutaric acid and adipic acid and having a nitric acid content of 3% by weight or less, based on the total weight of the succinic, glutaric and adipic acids, wherein the dicarboxylic acid mixture is prepared by denitrating an aqueous by-product solution obtained in an adipic acid production process, and (B) subjecting the dicarboxylic acid mixture to hydrogenation in the presence of water, hydrogen gas and a hydrogenation catalyst containing an active metal species comprising ruthenium and tin, to thereby obtain a hydrogenation reaction mixture comprising a diol mixture comprising 1,4-butanediol, 1,5-pentanediol and 1,6-hexanediol.

22 Claims, No Drawings

PROCESS FOR THE PREPARATION OF DIOL MIXTURES

This application is the national phase under 35 U.S.C. § 371 of PCT International Application No. PCT/JP00/07757 which has an International filing date of Nov. 2, 2000, which designated the United States of America.

BACKGROUND OF THE INVENTION

1. Field of the Invention

The present invention relates to a method for producing a diol mixture. More particularly, the present invention is concerned with a method for producing a diol mixture comprising 1,4-butanediol, 1,5-pentanediol and 1,6-hexanediol, which comprises: (A) providing a dicarboxylic acid mixture comprising succinic acid, glutaric acid and adipic acid and having a nitric acid content which does not exceed a specific value, wherein the dicarboxylic acid mixture is prepared by denitrating an aqueous by-product solution obtained in an adipic acid production process, and (B) subjecting the dicarboxylic acid mixture to hydrogenation in the presence of water, hydrogen gas and a hydrogenation catalyst containing an active metal species comprising ruthenium and tin, to thereby obtain a hydrogenation reaction mixture comprising a diol mixture comprising 1,4-butanediol, 1,5-pentanediol and 1,6-hexanediol. The method of the present invention for producing a diol mixture is advantageous not only in that an aqueous by-product solution (containing a dicarboxylic acid mixture comprising succinic acid, glutaric acid and adipic acid) obtained in an adipic acid production process can be used as a raw material for a useful diol mixture, but also in that a diol mixture comprising 1,4-butanediol, 1,5-pentanediol and 1,6-hexanediol can be produced stably for a long period of time directly from the dicarboxylic acids by hydrogenation thereof, not through esterification thereof.

2. Prior Art

Diols are very important compounds which are widely used as raw materials for polyester resins, urethane foams, urethane coating materials, adhesives and the like in various industrial fields. Diols are commercially produced in large amounts. The production of diols is conducted mainly by a method which comprises subjecting a dicarboxylic diester to hydrogenation. Hereinbelow, an explanation is made with respect to the production of diols by this method involving hydrogenation of a dicarboxylic diester, taking production of 1,4-butanediol as an example.

As a method for producing 1,4-butanediol, a method is known in which two hydroxyl groups are introduced into n-butane to thereby produce 1,4-butanediol. This method is very disadvantageous from an economical view-point. Therefore, at present, it is virtually impossible to produce 1,4-butanediol on a commercial scale by the above-mentioned method. For this reason, at present, 1,4-butanediol is produced from n-butane by a method comprising: subjecting n-butane to air oxidation to produce succinic acid, maleic acid, succinic anhydride or maleic anhydride, especially maleic acid or maleic anhydride: and producing 1,4-butanediol from the thus produced acid or acid anhydride.

In general, a dicarboxylic acid, such as maleic acid, can be easily converted to a diol by a reduction reaction. In the reduction reaction, generally, an appropriate reducing agent is used. Usually, the reduction reaction of a dicarboxylic acid requires the use of a strong reducing agent having extremely high reactivity, such as lithium aluminum hydride. Special care must be taken in the handling and storage of such a strong reducing agent. Therefore, such a strong reducing agent is not suitable for use in the commercial scale production of a diol.

On the other hand, the so-called hydrogenation reaction, i.e., a reduction reaction performed using hydrogen gas as a reducing agent in the presence of an appropriate catalyst, is suitable for practice on a commercial scale. However, usually, the hydrogenation reaction cannot be applied to the reduction of a dicarboxylic acid. This is because the conventional catalyst used for hydrogenation is soluble in a dicarboxylic acid, so that the catalytic activity of the catalyst cannot be maintained in the presence of a dicarboxylic acid.

Therefore, at present, the production of 1,4-butanediol is performed by a method in which maleic acid or maleic anhydride obtained by air oxidation of n-butane is reacted with an appropriate alcohol to obtain a maleic diester, and the obtained maleic diester is subjected to a hydrogenation reaction in the presence of a copper-containing catalyst under high temperature and high pressure conditions, to thereby convert the diester to 1,4-butanediol.

The method for producing an alcohol by the hydrogenation of an ester in the presence of a copper-containing catalyst under high temperature and high pressure conditions is described in, for example, Japanese Patent Application prior-to-examination Publication (Kohyo) No. 2000-510837 (corresponding to U.S. Pat. No. 6,100,410), Japanese Patent Application prior-to-examination Publication (Kohyo) No. 2000-510475 (corresponding to U.S. Pat. No. 6,077,964), Japanese Patent Application prior-to-examination Publication (Kohyo) No. 2000-506134 (corresponding to U.S. Pat. No. 5,981,769), Unexamined Japanese Patent Application Laid-Open Specification No. 7-196558 (corresponding to U.S. Pat. No. 5,414,159) and U.S. Pat. No. 5,334,779.

However, in any of the methods of these patent documents, three steps (i.e., production of a dicarboxylic acid, esterification of the produced dicarboxylic acid, and hydrogenation of the produced ester) are required, so that the process for producing an alcohol inevitably becomes complicated. The complicated process poses a problem in that the process needs a number of apparatuses, such as an apparatus for the esterification of the dicarboxylic acid and an apparatus for separating, recovering and recycling an alcohol which is by-produced in the step for hydrogenation of the ester, wherein the alcohol is that which has been used in the esterification of the dicarboxylic acid.

As is understood from the above, the production of a diol by the hydrogenation of a diester is disadvantageous from the viewpoint of the production cost and the like. Therefore, various studies have been made with respect to the method for simplifying the process for producing a diol.

As an example of such a method, there can be mentioned a method in which a dicarboxylic acid (but not an ester thereof) is directly subjected to hydrogenation using a catalyst which can maintain its catalytic activity even in the presence of an acid, to thereby obtain a diol.

In this method, a diol can be obtained by a two-step process, i.e., a process comprising the steps of producing a dicarboxylic acid and then hydrogenating the produced dicarboxylic acid. In this method, esterification of a dicarboxylic acid (such esterification is required in the conventional process) is not required, so that an apparatus for the esterification is not required. Further, since this method does not involve esterification, this method is free from the problem that an alcohol (used in the esterification) is by-produced in the hydrogenation of the ester, and therefore this method does not need an apparatus for recovering and recycling the by-produced alcohol. As a result, the process for producing a diol can be simplified, and plant and equipment required for practicing the process can also be considerably simplified.

A number of proposals have been made with respect not only to catalysts for use in the hydrogenation of a dicarboxylic acid to produce a diol and but also to methods for producing a diol using such catalysts. Some of these proposals are concerned with technologies for producing 1,4-butanediol by the direct hydrogenation of succinic acid or maleic acid. In these technologies, usually, the hydrogenation is performed in the presence of water. Only the catalyst systems used in these technologies are enumerated below.

A catalyst comprising a ruthenium-iron oxide (U.S. Pat. No. 4,827,001);

a catalyst comprising a porous carbon having carried thereon ruthenium-tin, wherein the BET specific surface area (as determined by the application of the Brunauer-Emmett-Teller adsorption isotherm) of the porous carbon is 2,000 m$^2$/g or more (Unexamined Japanese Patent Application Laid-Open Specification No. 5-246915);

a catalyst comprising silica having carried thereon ruthenium and tin, wherein the silica has been modified with titanium and/or alumina (Unexamined Japanese Patent Application Laid-Open Specification No. 6-116182);

a catalyst comprising a carrier having carried thereon ruthenium, tin and a compound selected from the group consisting of an alkali metal compound and an alkaline earth metal compound (Unexamined Japanese Patent Application Laid-Open Specification No. 6-239778);

a catalyst comprising a porous carrier having carried thereon tin and at least one metal selected from the group consisting of ruthenium, platinum and rhodium (Unexamined Japanese Patent Application Laid-Open Specification No. 7-165644);

a catalyst comprising a carrier having carried thereon ruthenium and tin (Unexamined Japanese Patent Application Laid-Open Specification No. 9-12492) (In the method using this catalyst, the hydrogenation is performed while feeding an excess amount of hydrogen gas into the reaction system and withdrawing, from the reaction system, the unreacted hydrogen gas and the hydrogenation product entrained thereby.);

a catalyst comprising a porous carrier having carried thereon ruthenium-tin-platinum (Unexamined Japanese Patent Application Laid-Open Specification No. 9-59190);

a catalyst comprising a carbonaceous carrier having carried thereon ruthenium-tin-platinum, wherein the catalyst is prepared by a method comprising impregnating a carbonaceous carrier with a solution containing a carbonyl compound having 5 or less carbon atoms and metal components to be carried on the carbonaceous carrier (Unexamined Japanese Patent Application Laid-Open Specification No. 10-15388); and a catalyst comprising a carbonaceous carrier having carried thereon ruthenium-tin-platinum, wherein the carbonaceous carrier, prior to having carried thereon the above metals, has been contacted with nitric acid (Unexamined Japanese Patent Application Laid-Open Specification No. 10-71332).

Unexamined Japanese Patent Application Laid-Open Specification No. 7-82190 proposes a method in which a dicarboxylic acid is subjected to hydrogenation in a tertiary alcohol as a solvent in the presence of a catalyst comprising palladium and a rhenium compound. On the other hand, U.S. Pat. No. 5,698,749 teaches that 1,4-butanediol can be produced from maleic acid in a relatively high yield by the use of a catalyst comprising an activated carbon having carried thereon palladium-silver-rhenium, wherein the activated carbon, prior to having carried thereon the metals, has been subjected to oxidation treatment with nitric acid. Furthermore, Unexamined Japanese Patent Application Laid-Open Specification No. 11-60523 (corresponding to U.S. Pat. No. 5,969,194) teaches that, when adipic acid is directly subjected to hydrogenation using a catalyst comprising an activated carbon having carried thereon ruthenium-tin-platinum, wherein the activated carbon, prior to having carried thereon the metals, has been subjected to acid treatment, 1,6-hexanediol can be obtained from adipic acid in high yield.

As described hereinabove, there are known a number of techniques for hydrogenating a dicarboxylic acid, such as succinic acid, maleic acid or adipic acid; however, each method is intended for hydrogenating a single dicarboxylic acid. Any of the above-mentioned patent documents has no description about a technique in which a mixture of a plurality of dicarboxylic acids is directly subjected to hydrogenation to thereby produce a mixture of a plurality of diols. An aqueous by-product solution containing a dicarboxylic acid mixture, wherein the aqueous by-product solution is obtained in an adipic acid production process, has little utility. However, if it becomes possible for such an aqueous by-product solution to be used as a raw material for a hydrogenation reaction to produce diols which are useful as raw materials for polyurethanes and polyesters, a great commercial advantage would be obtained. This point is more specifically described below.

Adipic acid is produced by a process in which a cyclic aliphatic compound, such as cyclohexanone or cyclohexanol, is subjected to oxidation with nitric acid to thereby obtain an aqueous reaction mixture containing adipic acid, and the adipic acid contained in the aqueous mixture is subjected to crystal deposition, and the deposited crystals are then isolated from the reaction mixture to obtain an aqueous by-product solution. This aqueous by-product solution is an aqueous solution containing a dicarboxylic acid mixture comprising succinic acid, glutaric acid and adipic acid. An esterification product of this aqueous by-product solution has been used as a solvent, but the demand for such an esterification product as a solvent is not so large and, therefore, at present, a part of the aqueous by-product solution is discarded as a waste. However, if the aqueous by-product solution containing a dicarboxylic acid mixture, wherein the by-product solution is obtained in an adipic acid production process, can be used as a raw material for a hydrogenation reaction, there can be produced diols (specifically 1,4-butanediol, 1,5-pentanediol and 1,6-hexanediol) which are useful as raw materials for polyurethanes and polyesters. This is a great commercial advantage.

However, in the studies by the present inventors, it has been found that, when an aqueous by-product solution containing a dicarboxylic acid mixture, wherein the by-product solution is obtained in an adipic acid production process, is directly subjected to hydrogenation, the catalytic activity of a catalyst used is markedly lowered in accordance with the lapse of the reaction time. Therefore, conventionally, there has not been practiced a method in which diols are produced on a commercial scale from an aqueous by-product solution containing a dicarboxylic acid mixture, wherein the by-product solution is obtained in an adipic acid production process.

SUMMARY OF THE INVENTION

In this situation, the present inventors have made extensive and intensive studies with a view toward developing a method for efficiently producing diols stably for a long period of time, in which an aqueous by-product solution containing a dicarboxylic acid mixture, wherein the by-product solution is obtained in an adipic acid production process, is used as a raw material for a hydrogenation reaction. As a result, it has unexpectedly been found that diols can be efficiently produced stably for a long period of time without a lowering of the catalytic activity of a catalyst, by a method which comprises: providing a dicarboxylic acid mixture having a nitric acid content which does not exceed a specific value, wherein the dicarboxylic acid mixture is prepared by denitrating an aqueous by-product solution obtained in an adipic acid production process; and subjecting the dicarboxylic acid mixture to hydrogenation in the presence of a hydrogenation catalyst containing an active metal species comprising ruthenium and tin. Further, it has also unexpectedly been found that, in the above-mentioned method, the stability of the diol production can be further increased (i.e., efficient diol production can be performed for a longer period of time) by performing an additional step for reducing to a specific level or less the amounts of further impurities, such as metal values (e.g. copper values and vanadium values) and sulfur values, which are contained in the dicarboxylic acid mixture. Based on these novel findings, the present invention has been completed.

Accordingly, it is a primary object of the present invention to provide a method for efficiently producing diols stably for a long period of time, in which an aqueous by-product solution containing a dicarboxylic acid mixture is used as a raw material for a hydrogenation reaction, wherein the aqueous by-product solution is obtained in an adipic acid production process including a step of subjecting at least one $C_6$ cyclic aliphatic compound to oxidation with nitric acid.

The foregoing and other objects, features and advantages of the present invention will be apparent from the following detailed description and appended claims.

DETAILED DESCRIPTION OF THE INVENTION

In one aspect of the present invention, there is provided a method for producing a diol mixture comprising 1,4-butanediol, 1,5-pentanediol and 1,6-hexanediol, which comprises:

(A) providing a dicarboxylic acid mixture comprising succinic acid, glutaric acid and adipic acid and having a nitric acid content of 3% by weight or less, based on the total weight of the succinic, glutaric and adipic acids,
the dicarboxylic acid mixture being prepared by denitrating an aqueous by-product solution obtained in an adipic acid production process comprising subjecting at least one $C_6$ cyclic aliphatic compound to oxidation with nitric acid in an aqueous medium in the presence of an oxidation catalyst to thereby obtain an aqueous reaction mixture comprising succinic acid, glutaric acid and adipic acid, depositing crystals of the adipic acid, and isolating the deposited crystals from the reaction mixture to obtain the aqueous by-product solution; and (B) subjecting the dicarboxylic acid mixture to hydrogenation in the presence of water, hydrogen gas and a hydrogenation catalyst containing an active metal species comprising ruthenium and tin, to thereby obtain a hydrogenation reaction mixture comprising a diol mixture comprising 1,4-butanediol, 1,5-pentanediol and 1,6-hexanediol.

For easy understanding of the present invention, the essential features and various preferred embodiments of the present invention are enumerated below.

1. A method for producing a diol mixture comprising 1,4-butanediol, 1,5-pentanediol and 1,6-hexanediol, which comprises:

(A) providing a dicarboxylic acid mixture comprising succinic acid, glutaric acid and adipic acid and having a nitric acid content of 3% by weight or less, based on the total weight of the succinic, glutaric and adipic acids,
   the dicarboxylic acid mixture being prepared by denitrating an aqueous by-product solution obtained in an adipic acid production process comprising subjecting at least one $C_6$ cyclic aliphatic compound to oxidation with nitric acid in an aqueous medium in the presence of an oxidation catalyst to thereby obtain an aqueous reaction mixture comprising succinic acid, glutaric acid and adipic acid, depositing crystals of the adipic acid, and isolating the deposited crystals from the reaction mixture to obtain the aqueous by-product solution; and (B) subjecting the dicarboxylic acid mixture to hydrogenation in the presence of water, hydrogen gas and a hydrogenation catalyst containing an active metal species comprising ruthenium and tin, to thereby obtain a hydrogenation reaction mixture comprising a diol mixture comprising 1,4-butanediol, 1,5-pentanediol and 1,6-hexanediol.

2. The method according to item 1 above, wherein, before step (B), the dicarboxylic acid mixture is adjusted to satisfy at least one condition selected from the group consisting of the following conditions (1) to (3):

(1) the mixture has a nitric acid content of 0.2% by weight or less, based on the total weight of the succinic, glutaric and adipic acids;

(2) the mixture has a copper content of 10 ppm by weight or less and a vanadium content of 10 ppm by weight or less, each based on the total weight of the succinic, glutaric and adipic acids; and (3) the mixture has a sulfur content of 200 ppm by weight or less, based on the total weight of the succinic, glutaric and adipic acids.

3. The method according to item 2 above, wherein, in the condition (3), the mixture has a sulfur content of 40 ppm by weight or less, based on the total weight of the succinic, glutaric and adipic acids.

4. The method according to any one of items 1 to 3 above, wherein the dicarboxylic acid mixture in the form of a solution thereof in distilled water exhibits an absorption coefficient of 0.3 or less as measured at 355 nm, wherein the absorption coefficient is determined by the following formula:

$$E=A/(c \times b)$$

wherein E represents the absorption coefficient as measured at 355 nm,

A represents the absorbance of the solution of the dicarboxylic acid mixture in distilled water at room temperature, c represents the amount (g) of the dicarboxylic acid mixture dissolved in 100 g of distilled water, and b represents the length (cm) of a cell used for measuring the absorbance.

5. The method according to item 4 above, wherein the dicarboxylic acid mixture in the form of a solution thereof in distilled water exhibits an absorption coefficient of 0.1 or less.

6. The method according to any one of items 1 to 5 above, wherein the dicarboxylic acid mixture contains an impurity component having an oxygen-nitrogen bond in an amount of 2,000 ppm by weight or less in terms of the amount of nitric acid, based on the total weight of the succinic, glutaric and adipic acids.

7. The method according to any one of items 1 to 6 above, wherein the active metal species contained in the hydrogenation catalyst further comprises at least one metal selected from the group consisting of metals of Group 7 of the Periodic Table.

8. The method according to item 7 above, wherein the at least one metal selected from the group consisting of metals of Group 7 of the Periodic Table is rhenium.

9. The method according to any one of items 1 to 8 above, wherein the active metal species contained in the hydrogenation catalyst further comprises at least one metal selected from the group consisting of metals of Group 8 of the Periodic Table other than ruthenium and metals of Groups 9 and 10 of the Periodic Table.

10. The method according to item 9 above, wherein the at least one metal selected from the group consisting of metals of Group 8 of the Periodic Table other than ruthenium and metals of Groups 9 and 10 of the Periodic Table, is platinum.

11. The method according to any one of items 1 to 10 above, wherein the hydrogenation catalyst further comprises an activated carbon having carried thereon the active metal species.

12. The method according to any one of items 1 to 11 above, wherein the hydrogenation is conducted under conditions wherein the temperature is from 100 to 300° C. and the hydrogen pressure is from 1 to 25 MPa.

13. The method according to any one of items 1 to 12 above, wherein the dicarboxylic acid mixture is prepared in the form of an aqueous solution thereof by a first purification process comprising the steps of:

(a) heating the aqueous by-product solution at a temperature of from 80 to 200° C. under atmospheric or lower pressure to effect dehydration and denitration of the aqueous by-product solution to obtain a dehydrated and denitrated dicarboxylic acid mixture;

(b) adding water to the obtained dehydrated and denitrated dicarboxylic acid mixture to thereby obtain an aqueous denitrated dicarboxylic acid mixture solution; and (c) contacting the aqueous denitrated dicarboxylic acid mixture solution with a cation exchange resin to thereby remove copper values and vanadium values.

14. The method according to item 13 above, wherein the first purification process further comprises step (d) of contacting the aqueous denitrated dicarboxylic acid mixture solution with an anion adsorptive substance.

15. The method according to item 13 or 14 above, wherein the first purification process further comprises the step of contacting the aqueous denitrated dicarboxylic acid mixture solution with an activated carbon.

16. The method according to any one of items 1 to 12 above, wherein the dicarboxylic acid mixture is prepared by a second purification process comprising the steps of:

(a) heating the aqueous by-product solution at a temperature of from 80 to 130° C. under atmospheric or lower pressure, followed by heating at a temperature of from higher than 130° C. to 180° C. under atmospheric pressure, to thereby obtain a dehydrated and denitrated dicarboxylic acid mixture;

(b) adding water to the obtained dehydrated and denitrated dicarboxylic acid mixture to thereby obtain an aqueous denitrated dicarboxylic acid mixture solution;

(c) contacting the aqueous denitrated dicarboxylic acid mixture solution with a cation exchange resin to thereby remove copper values and vanadium values;

(d) heating the resultant aqueous denitrated dicarboxylic acid mixture solution under atmospheric or lower pressure at a temperature sufficient to distill off water from the resultant aqueous denitrated dicarboxylic acid mixture solution and obtain a denitrated dicarboxylic acid mixture;

(e) adding a $C_6$–$C_{14}$ aromatic hydrocarbon having a boiling point of 200° C. or less under atmospheric pressure to the denitrated dicarboxylic acid mixture obtained in step (d), and heating the resultant mixture at a temperature which is not higher than the boiling point of the aromatic hydrocarbon, followed by cooling: and (f) recovering the denitrated dicarboxylic acid mixture from the mixture by filtration, thereby preparing the dicarboxylic acid mixture.

17. The method according to item 16 above, wherein the second purification process further comprises, after step (a), the step of contacting the aqueous denitrated dicarboxylic acid mixture solution or an aqueous solution of the denitrated dicarboxylic acid mixture in water, with an anion adsorptive substance.

18. The method according to any one of items 1 to 12 above, wherein the dicarboxylic acid mixture is prepared in the form of an aqueous solution thereof by a third purification process comprising:

contacting the aqueous by-product solution with hydrogen gas in the presence of a reduction catalyst containing an active metal species comprising at least one metal selected from the group consisting of metals of Groups 7 to 10 of the Periodic Table, to thereby reduce nitric acid and an impurity component having an oxygen-nitrogen bond contained in the aqueous by-product solution, thereby obtaining the dicarboxylic acid mixture in the form of an aqueous solution thereof.

19. The method according to item 18 above, wherein the reduction of the nitric acid and an impurity component having an oxygen-nitrogen bond in the third purification process is conducted under conditions wherein the temperature is from 50 to 200° C. and the hydrogen pressure is from 0.2 to 5 MPa.

20. The method according to item 18 or 19 above, wherein the active metal species contained in the reduction catalyst used in the third purification process is at least one metal selected from the group consisting of platinum, rhenium, palladium, rhodium, nickel, iridium and ruthenium.

21. The method according to any one of items 18 to 20 above, wherein, prior to the contacting of the aqueous by-product solution with hydrogen gas in the third purification process, the aqueous by-product solution is heated at a temperature of from 80 to 130° C. under atmospheric or lower pressure and then heated at a temperature of from higher than 130° C. to 180° C. under atmospheric pressure, followed by addition of water thereto.

22. A method for recovering 1,4-butanediol and a mixture of 1,5-pentanediol and 1,6-hexanediol from the diol mixture obtained by the method of any one of items 1 to 21 above, which comprises:
  (i) adjusting the temperature of the hydrogenation reaction mixture comprising the diol mixture to a temperature of from room temperature to less than 100° C., followed by a gas-liquid separation under atmospheric or lower pressure under which water is not boiled at the adjusted temperature of the mixture to remove the hydrogen gas from the hydrogenation reaction mixture;
  (ii) heating the hydrogen gas-removed hydrogenation reaction mixture under atmospheric pressure to thereby distill off the water and a mixture of cyclic ethers and monohydric alcohols which is by-produced in the hydrogenation reaction;
  (iii) subjecting the resultant mixture to multi-stage distillation to distill off the water and γ-butyrolactone by-produced in the hydrogenation reaction, thereby obtaining a purified diol mixture;
  (iv) subjecting the purified diol mixture to multi-stage distillation to obtain 1,4-butanediol as a low boiling point component while withdrawing a high boiling point mixture; and
  (v) subjecting the high boiling point mixture withdrawn in step (iv) to multi-stage distillation to obtain a mixture of 1,5-pentanediol and 1,6-hexanediol as a distillate.

Hereinbelow, the present invention will be described in detail.

Adipic acid is produced by a process comprising subjecting at least one $C_6$ cyclic aliphatic compound, such as cyclohexanone and cyclohexanol, to oxidation with nitric acid in the presence of an oxidation catalyst comprising copper and vanadium. In such a process, in addition to adipic acid which is a desired compound, other dicarboxylic acids, i.e., succinic acid, glutaric acid, malonic acid and oxalic acid, and a small amount of a tinting substance are formed as by-products. These by-products exhibit a high solubility in water. Therefore, simply by cooling a reaction mixture obtained by the above-mentioned oxidation to room temperature or lower, deposition of crystals of adipic acid in the reaction mixture occurs. The deposited crystals of the adipic acid are isolated from the reaction mixture by filtration, wherein the resultant filtrate (aqueous by-product solution) contains the above-mentioned by-products, as well as nitric acid and oxidation catalyst. Generally, this aqueous by-product solution is condensed, followed by addition of an appropriate amount of further nitric acid, and the resultant is recycled to the reaction system for producing adipic acid. However, when the recycle of the aqueous by-product solution is repeated, the by-product concentration of the reaction mixture is increased, thereby lowering the purity of the desired adipic acid.

In order to prevent the lowering of the purity of adipic acid, generally, a part of the aqueous by-product solution is withdrawn from the production system for adipic acid. From the withdrawn aqueous by-product solution, useful components are recovered, wherein, for example, the nitric acid is recovered by distillation, and the catalyst is recovered by ion-exchange. The remainder of the by-product solution is recovered as an aqueous by-product solution containing a dicarboxylic acid mixture. The aqueous by-product solution containing a dicarboxylic acid mixture is comprised mainly of succinic acid, glutaric acid and adipic acid which has not been recovered. Conventionally, these dicarboxylic acids are esterified and the resultant esters are used as solvents and the like.

By contrast, in the present invention, as a raw material in the process for producing a diol mixture, an aqueous by-product solution obtained in an adipic acid production process is used, wherein the adipic acid production process comprises subjecting at least one $C_6$ cyclic aliphatic compound to oxidation with nitric acid in an aqueous medium in the presence of an oxidation catalyst to thereby obtain an aqueous reaction mixture, depositing crystals of the adipic acid in the reaction mixture, and isolating the deposited crystals from the reaction mixture to obtain the aqueous by-product solution. In the present invention, the aqueous by-product solution may be either an aqueous solution obtained by removing adipic acid from the above-mentioned reaction mixture obtained in the adipic acid production process or an aqueous solution obtained by recovering, from the above-mentioned reaction mixture, useful components (such as the nitric acid and the catalyst) as well as the adipic acid. In the aqueous by-product solution used in the present invention, the concentration of the dicarboxylic acids is generally from 5 to 40% by weight, and the dicarboxylic acids contained therein mainly include succinic acid and glutaric acid which have been by-produced, and adipic acid which has not been recovered. In the aqueous by-product solution, generally, the concentrations of succinic acid, glutaric acid and adipic acid are, respectively, from about 15 to about 35% by weight, from about 45 to about 75% by weight and from about 3 to about 40% by weight, each based on the total weight of succinic acid, glutaric acid and adipic acid. In addition, the aqueous by-product solution contains nitric acid which has not been recovered, copper and/or vanadium derived from the catalyst used in the oxidation using nitric acid, and small amounts of other impurities. The nitric acid content of the aqueous by-product solution varies depending on the conditions employed for recovering the nitric acid, but is generally about 6% by weight or more, based on the total weight of succinic acid, glutaric acid and adipic acid. Further, the aqueous by-product solution assumes a yellow color which is considered to be due to the impurities present in the solution.

In the present invention, as mentioned above, the diol mixture is produced using the aqueous by-product solution obtained in the above-mentioned adipic acid production process. More specifically, the diol mixture is produced by providing a dicarboxylic acid mixture which is prepared by denitrating the aqueous by-product solution to adjust the nitric acid content of the solution to 3% by weight or less, based on the total weight of the succinic, glutaric and adipic acids, followed by subjecting the dicarboxylic acid mixture to hydrogenation.

With respect to the dicarboxylic acid mixture used in the present invention, the nitric acid content thereof is 3% by weight or less, preferably 0.2% by weight or less, more preferably 0.05% by weight or less, based on the total weight of the succinic, glutaric and adipic acids. It is most preferred that the nitric acid is completely removed from the dicarboxylic acid mixture; however, it is not practical to completely remove the nitric acid, since it is necessary to repeatedly conduct a treatment, such as a heat treatment or a treatment using an ion exchange resin. In a treatment generally conducted, it is difficult to achieve a lowering of the nitric acid content to a level as low as less than about 0.01 ppm. When the nitric acid content of the dicarboxylic acid mixture is more than 3% by weight, the activity of the hydrogenation catalyst used in the production of the diol mixture is lowered with time, so that it becomes impossible to produce the diol mixture stably for a long period of time. The influence of the nitric acid on the hydrogenation reaction has not yet been elucidated, but it is considered that a part of the metal species of the hydrogenation catalyst is eluted under the influence of the nitric acid to thereby lower the catalytic activity. Whether or not the elution of the metal species occurs due to the presence of nitric acid depends on the atmosphere in which the catalyst is present. For example, it is known that a stainless steel has a passive film formed on the surface thereof and, hence, will not be corroded even in the presence of nitric acid. However, it is considered that, under the hydrogenation conditions employed in the present invention, since the catalyst is present in a reducing atmosphere containing hydrogen, the passive film on the surface of a metal becomes unstable to cause the elution of the metal in the presence of nitric acid.

With respect to the removal of nitric acid from the aqueous by-product solution obtained in the adipic acid production process, any of the conventional methods can be employed. As an example of the method for removing nitric acid from the aqueous by-product solution, there can be mentioned a method in which the aqueous by-product solution is heated at a temperature of from 80 to 200° C. under atmospheric or lower pressure which is not less than about 80 kPa. More specifically, in this method, by heating the aqueous by-product solution in an evaporator at a temperature of from 80 to 130° C. under atmospheric or less pressure which is not less than 80 kPa, the nitric acid is removed together with water by azeotropic distillation. In this case, when the amount of water is smaller than that of nitric acid, the nitric acid concentration in the evaporator after removal of all of the water by azeotropic distillation becomes high. The high nitric acid concentration in the evaporator does not necessarily cause a problem; however, for continuing the azeotropic distillation after removal of all of the water, it is preferred that the removal of nitric acid by azeotropic distillation is conducted while adding water to the evaporator. As another example of the method for removing nitric acid from the aqueous by-product solution, there can be mentioned a method in which the aqueous by-product solution is heated at a temperature of from 100 to 200° C., preferably from 130 to 180° C., under approximately atmospheric pressure to distill off nitric acid from the aqueous by-product solution. In this method, at an initial stage of the distillation, nitric acid is distilled in the form of an azeotropic mixture thereof with water. As a further example of the method for removing nitric acid form the aqueous by-product solution, there can be mentioned a method using an anion exchange resin. The above-mentioned methods can be used individually or in combination. Especially preferred for removing nitric acid from the aqueous by-product solution is a method in which the aqueous by-product solution is heated at a temperature of from 100 to 130° C. under atmospheric pressure for 10 minutes to 3 hours to distill off most of nitric acid and water, followed by heating at a temperature of from higher than 130° C. to 200° C., preferably from 160 to 180° C., for 1 minute to 1 hour. This method is simple and, hence, is preferred. In this method, especially by heating at a temperature of from 160 to 180° C., not only nitric acid but also a part of the below-described impurity component having an oxygen-nitrogen bond can be removed. Further, with respect to this especially preferred method, the reason why the heating is conducted in two stages is that the desirable time for heating differs between the heating conducted at a temperature of from 100 to 130° C. and the heating conducted at a temperature of from higher than 130° C. to 200° C. The above-method using an anion exchange resin is also effective; however, when the amount of nitric acid to be removed is large, it becomes necessary to use a large amount of an anion exchange resin, so that large amount of labor becomes necessary to regenerate the anion exchange resin. The method using an anion exchange resin is effective for removing nitric acid which is present in a very small amount. Further, when the nitric acid content of the aqueous by-product solution is from several % by weight to about 10% by weight, it is also possible to use a method in which nitric acid is neutralized by a hydroxide, carbonate, hydrogencarbonate or the like of an alkali metal or an alkaline earth metal (e.g., caustic soda).

Alternatively, by subjecting the aqueous by-product solution to reduction treatment, it is possible to remove nitric acid together with the impurity component having an oxygen-nitrogen bond. Specifically, the nitric acid and the impurity component having an oxygen-nitrogen bond, which are contained in the aqueous by-product solution, can be removed by subjecting the aqueous by-product solution to a reduction treatment comprising contacting the aqueous by-product solution with hydrogen gas in the presence of a reduction catalyst containing an active metal species comprising at least one metal selected from the group consisting of metals of Groups 7 to 10 of the Periodic Table, to thereby reduce and/or decompose the nitric acid and the impurity component having an oxygen-nitrogen bond. The conditions for the reduction treatment are not particularly limited so long as the nitric acid is removed and neither reduction nor decomposition of the dicarboxylic acids occurs. However, it is preferred that the reduction treatment is conducted at a temperature of from 50 to 200° C., more advantageously from 100 to 180° C. When the reduction treatment is conducted at a temperature lower than 50° C., it is likely that the reaction rate becomes low, so that a very long time is needed to effect the reduction satisfactorily. On the other hand, when the reduction treatment is conducted at a temperature higher than 200° C., it is likely that the dicarboxylic acids are also reduced or decomposed depending on the time of the treatment. With respect to the hydrogen gas pressure for the reduction treatment, the hydrogen gas pressure is preferably from 0.2 to 5 MPa, more preferably from 1 to 4 MPa. When the hydrogen gas pressure is lower than 0.2 MPa, it becomes difficult to effect the reduction satisfactorily. On the other hand, when the hydrogen gas pressure is higher than 5 MPa, disadvantages are likely to be caused that it is necessary to use an expensive apparatus for conducting the reduction treatment, and that the dicarboxylic acids are decomposed. The time needed for the reduction treatment is generally from several minutes to several tens of hours, preferably 10 minutes to 5 hours. With respect to the manner for contacting the aqueous by-product solution with hydrogen gas, there is no particular limitation. For example, the contacting can be effected either in a batchwise manner using an agitation vessel or in a continuous manner using a fixed-bed reaction column.

With respect to the reduction catalyst used in the reduction treatment for removal of nitric acid, which contains an active metal species comprising at least one metal selected from the group consisting of metals of Groups 7 to 10 of the Periodic Table, such a catalyst is generally used in a hydrogenation reaction. It is preferred that the active metal species contained in the reduction catalyst is at least one metal selected from the group consisting of platinum, rhenium, palladium, rhodium, nickel, iridium and ruthenium. From the viewpoint of the activity of the reduction catalyst, it is more preferred that the active metal species contained in the reduction catalyst is at least one metal selected from the group consisting of platinum, rhenium, palladium, rhodium, and ruthenium. From the viewpoint of the durability of the catalyst as well as the activity of catalyst, it is most preferred that the active metal species contained in the reduction catalyst comprises platinum.

In the present invention, the "Periodic Table" means the Periodic Table proposed by the American Chemical Society, Division of Inorganic Chemistry in 1985.

In the present invention, the reduction catalyst may comprise a carrier having carried thereon the active metal species. Examples of carriers include porous carriers, such as an activated carbon, diatomaceous earth, silica, alumina, titania and zirconia. These porous carriers may be used individually or in combination. As a method for causing the active metal species to be carried on the carrier, there can be used any of the conventional methods generally used for producing a catalyst comprising a carrier having carried thereon a catalyst component. Examples of such conventional methods include a dipping method and an ion exchange method. The metal compounds used as sources for the active metal species may vary depending on the method for producing the catalyst. Representative examples of metal compounds include an inorganic acid salt, such as a nitrate, a sulfate, and a chloride; an organic acid salt, such as an acetate; a hydroxide; an oxide; and an organometallic compound. In the reduction catalyst comprising a carrier having carried thereon the active metal species, the amount of the active metal species is 0.5 to 50% by weight, based on the weight of the carrier.

Further, as the reduction catalyst for removing nitric acid, it is also possible to use a catalyst containing an active metal species comprising ruthenium and tin, which is described below in detail and is used as a hydrogenation catalyst in the hydrogenation for producing the diol mixture. In this case, the catalyst which has been used in the reduction treatment, as such, can be used in the hydrogenation. However, generally, when a catalyst is used for a long period of time, it is possible that a lowering of the catalytic activity occurs. Therefore, in the present invention, separately supplied catalysts are generally used in the reduction treatment and the hydrogenation, respectively. When the reduction treatment of the aqueous by-product solution is conducted in a batchwise manner using an agitation vessel, it is preferred to use the reduction catalyst in an amount of 0.01 to 50 parts by weight, relative to 100 parts by weight of the aqueous by-product solution. The amount of the reduction catalyst can be appropriately selected in accordance with the reduction treatment conditions, such as a treatment temperature and a treatment pressure.

Further, it is preferred that, with respect to the dicarboxylic acid mixture used in the present invention, the copper content thereof is controlled to 10 ppm by weight or less, more advantageously 5 ppm by weight or less, and the vanadium content thereof is controlled to 10 ppm by weight or less, more advantageously 5 ppm by weight or less, each based on the total weight of succinic, glutaric and adipic acids. The forms of the compounds containing copper and vanadium, which are present in the aqueous by-product solution, are not clearly known. In the present invention, the copper content and the vanadium content are, respectively, measured in terms of the amounts of a copper atom and a vanadium atom. Each of copper and vanadium is derived from the oxidation catalyst used in the adipic acid production process. When a diol mixture is produced using as a raw material a dicarboxylic acid mixture having high contents of copper and vanadium, the copper and vanadium values are accumulated on the active metal species of the hydrogenation catalyst to decrease the surface area of the catalyst, so that the activity of the catalyst is lowered. It is most preferred that the copper and vanadium values are completely removed from the dicarboxylic acid mixture; however, it is not practical to completely remove the copper and vanadium values, since it is necessary to repeatedly conduct a treatment, such as a treatment using a cation exchange resin. In a treatment generally conducted, it is difficult to decrease each of the copper content and the vanadium content to lower than about 0.05 ppm.

With respect to a method for the removal of the copper and vanadium values contained in the aqueous by-product solution obtained in the adipic acid production process, there is no particular limitation, and any of the conventionally known methods can be used. However, a method using a cation exchange resin is preferred, because the copper and vanadium values can be easily removed and the formation of a waste by-product can be suppressed. Illustratively stated, in the method using a cation exchange resin, an aqueous by-product solution (or an aqueous solution obtained by addition of ion-exchanged water to a solid dicarboxylic acid mixture which is, as explained below, obtained during the purification of the aqueous by-product solution) is contacted with the cation exchange resin at a temperature of from room temperature to 100° C., to thereby remove the copper and vanadium values. As the cation exchange resin, a styrene polymer or a methacrylic polymer, which has a sulfonic acid group or a carboxyl group as a functional group, can be used. Such a cation exchange resin is contacted with the aqueous by-product solution (or the above-mentioned aqueous solution obtained by adding ion-exchanged water) by agitation-mixing or by using a packed column having packed therein a cation exchange resin, wherein the cation exchange resin is used in an amount of from 1 to 100 parts by weight per 100 parts by weight of the dicarboxylic acids contained.

Further, with respect to the dicarboxylic acid mixture used in the present invention, the sulfur content thereof is preferably controlled to 200 ppm by weight or less, more preferably to 40 ppm by weight or less, most preferably to 20 ppm by weight or less, based on the total weight of the succinic, glutaric and adipic acids. When a diol mixture is produced using as a raw material a dicarboxylic acid mixture having a high sulfur content, sulfur compounds are accumulated on the active metal species of the hydrogenation catalyst to decrease the surface area of the catalyst, so that the activity of the catalyst is lowered. It is most preferred that the sulfur values are completely removed from the dicarboxylic acid mixture; however, it is not practical to completely remove the sulfur values, since it is necessary to repeatedly conduct a treatment, such as a treatment using an anion exchange resin. In a treatment generally conducted, it is difficult to reduce the sulfur content of a level as low as less than about 0.2 ppm.

In the dicarboxylic acid mixture, the sulfur values are considered to be present in the form of sulfate group-containing compounds or the like; however, actually, the forms of sulfur-containing compounds present in the dicarboxylic acid mixture are not clearly known. Further, the reason why the sulfur values are contained in the dicarboxylic acid mixture is also not clearly known. However, it is presumed that, when a cation exchange resin having a sulfonic acid group is used for removing copper values and vanadium values, sulfur-containing impurities are eluted into the dicarboxylic acid mixture by liberation of the sulfonic groups or decomposition of the sulfonic group-containing polymer chain of the cation exchange resin. This presumption is supported by the fact that the sulfur values can be removed by an anion exchange resin.

With respect to a method for the removal of the sulfur-containing compounds from the aqueous by-product solution obtained in the adipic acid production process, there is no particular limitation. However, the removal of the sulfur-containing compounds can be effectively performed by a method in which the aqueous by-product solution is contacted with an anion exchange resin. In this method, when the removal of the sulfur-containing compounds is conducted with respect to a solid dicarboxylic acid mixture (which is, as explained below, obtained during the purification of the aqueous by-product solution), anion-exchanged water is added to the dicarboxylic acid mixture to obtain an aqueous solution containing 5 to 50% by weight of the dicarboxylic acid mixture, and the obtained aqueous solution is contacted with an anion exchange resin. As the anion exchange resin, it is preferred to use a styrene polymer or an acrylic polymer, which has a quaternary ammonium salt as a functional group. Further, if desired, a weakly basic ion exchange resin can also be used. As the weakly basic ion exchange resin, a styrene polymer or an acrylic polymer, which has a tertiary amine as a functional group, can be used. In the method using an anion exchange resin, the anion exchange resin is contacted with the dicarboxylic acid mixture by agitation-mixing or by using a packed column having the anion exchange resin packed therein, wherein the anion exchange resin is used in an amount of 1 to 100 parts by weight per 100 parts by weight of the dicarboxylic acid mixture.

Further, in the present invention, it is preferred that the dicarboxylic acid mixture in the form of a solution thereof in distilled water exhibits an absorption coefficient of advantageously 0.3 or less, more advantageously 0.1 or less, most advantageously 0.03 or less, as measured at 355 nm, wherein the absorption coefficient is determined by the following formula:

$$E=A/(c\times b)$$

wherein E represents the absorption coefficient as measured at 355 nm,

A represents the absorbance of the solution of the dicarboxylic acid mixture in distilled water at room temperature, c represents the amount (g) of the dicarboxylic acid mixture dissolved in 100 g of distilled water, and b represents the length (cm) of a cell used for measuring the absorbance.

The absorption observed at 355 nm is not ascribed to succinic, glutaric and adipic acids. Therefore, it is apparent that this absorption is ascribed to an impurity contained in the dicarboxylic acid mixture. The present inventors have not yet determined the molecular structure of this impurity; however, from the literature (for example, Zh. Prikl. Khim. Leningrad, Vol.47, No.4, p.862–865, 1974), it is considered that the impurity is any one of dinitrophenols (such as 2,5-dinitrophenol, 2,4-dinitrophenol, and 2,6-dinitrophenol), trinitrophenols, 1-nitrocyclohexene, and 2-nitrocyclohexenol, or a mixture thereof, and that the impurity is by-produced during the oxidation conducted using nitric acid in the adipic acid production process. As described above, each dicarboxylic acid in the dicarboxylic acid mixture, which is a raw material for the production of a diol mixture, exhibits no absorption at 355 nm. Therefore, it is most preferred that the above-mentioned absorption coefficient as measured at 355 nm is 0. However, it is not practical to obtain an absorption coefficient of 0 as measured at 355 nm, since it is necessary to repeatedly conduct a treatment, such as a treatment using an activated carbon or an ion exchange resin, which is very cumbersome. In a treatment generally conducted, it is difficult to decrease the absorption coefficient at 355 nm to a level of lower than about 0.0001.

With respect to a method for removing the impurity which exhibits an absorption as measured at 355 nm, there is no particular limitation, and any of the conventional decoloring methods can be used. For example, the removal of the impurity can be conducted by a method in which the aqueous by-product solution is treated with an anion adsorptive substance, followed by heating at 120 to 200° C. (see Examined Japanese Patent application Publication No. 53-41652). Examples of anion adsorptive substances include an activated carbon, an anion exchange resin and a liquid anion-exchanger. The liquid anion-exchanger is at least one amine selected from a group consisting of primary, secondary and tertiary water-insoluble amines, having a molecular weight of from 200 to 500.

For example, the removal of the impurity by using an activated carbon can be conducted as follows. A powdery or granular activated carbon is mixed with the aqueous by-product solution, wherein the activated carbon is used in an amount of from 1 to 20 parts by weight per 100 parts by weight of the dicarboxylic acids contained in the aqueous by-product solution, and the resultant mixture is stirred for 5 minutes to 2 hours, followed by separation of the activated carbon by filtration. With respect to the removal of the impurity by using an anion exchange resin, the removal of the impurity can be conducted in the same manner as in the removal of the sulfur values by using an anion exchange resin, which is explained above. The removal of the impurity by using a liquid anion-exchanger can be conducted as follows. A liquid anion-exchanger, such as tri-n-octylamine, is dissolved in a water-insoluble organic solvent to obtain an adsorptive solution having a liquid anion-exchanger content of from 0.1 to 10% by weight, and the resultant adsorptive solution is contacted with the aqueous by-product solution, wherein the liquid anion-exchanger is used in an amount of from 1 to 30% by weight, based on the weight of the dicarboxylic acids contained in the aqueous by-product solution. As examples of appropriate water-insoluble organic solvents, there can be mentioned carbon tetrachloride, Perclene, Trichlene and a liquid paraffin. The contacting of the adsorptive solution with the aqueous by-product solution can be conducted using an apparatus which is generally employed for a liquid-to-liquid contact. Examples of such apparatuses include an extraction column and a mixer-settler extractor.

Further, the present inventors have found that the absorption coefficient can be lowered by a treatment which comprises adding a $C_6$–$C_{14}$ aromatic hydrocarbon having a boiling point of 200° C. or less (as measured under atmospheric pressure) to a dehydrated and denitrated dicarboxylic acid mixture, heating the resultant mixture at a temperature which is not higher than the boiling point of the aromatic hydrocarbon, followed by cooling, and recovering from the resultant mixture the dehydrated and denitrated dicarboxylic acid mixture by filtration. By the above-mentioned treatment of the dehydrated and denitrated dicarboxylic acid mixture with an aromatic hydrocarbon, sulfur values can also be removed from the denitrated dicarboxylic acid mixture. Therefore, the treatment with an aromatic hydrocarbon can be employed instead of the above-mentioned treatment for removing sulfur values with an anion exchange resin. Examples of $C_6$–$C_{14}$ aromatic hydrocarbons having a boiling point of 200° C. or less, which can be used in this treatment, include benzene, toluene, xylene, ethylbenzene, isopropylbenzene, propylbenzene, trimethylbenzene and butylbenzene. Of these, benzene, toluene and xylene are preferred for the following reason. Each of benzene, toluene and xylene has a low boiling point. Therefore, even if any of these aromatic hydrocarbons remain in the dicarboxylic acid mixture which has been recovered by filtration, the aromatic hydrocarbons can be easily removed from the dicarboxylic acid mixture by, for example, heating under a reduced pressure. It is preferred that the amount of the aromatic hydrocarbon used is 0.5 to 20 times the total weight of succinic, glutaric and adipic acids contained in the dicarboxylic acid mixture. When the amount of the aromatic hydrocarbon is less than 0.5 time the total weight of the succinic, glutaric and adipic acids, the effect of decoloration of the dicarboxylic acid mixture becomes markedly lowered. As the amount of the aromatic hydrocarbon is increased, the effect of decoloration of the dicarboxylic acid mixture tends to be increased. However, when the amount of the aromatic hydrocarbon is larger than 20 times the total weight of the succinic, glutaric and adipic acids, the effect of decoloration cannot be improved any longer, as compared to the case where the amount of the aromatic hydrocarbon is 20 times. Therefore, in such a case, only a disadvantage is caused that the amount of the aromatic hydrocarbon which needs to be recovered and treated for recycling is increased.

Further, it is noted that the tinting substances (which include the below-mentioned impurity component having an oxygen-nitrogen bond) can also be removed from the aqueous by-product solution by the above-mentioned reduction treatment for denitration. Specifically, the tinting substances can be removed from the aqueous by-product solution by contacting the aqueous by-product solution with hydrogen gas in the presence of a reduction catalyst containing an active metal species comprising at least one metal selected from the group consisting of metals of Groups 7 to 10 of the Periodic Table, thereby reducing and/or decomposing the tinting substances.

Further, in the present invention, it is preferred that the dicarboxylic acid mixture contains an impurity component having an oxygen-nitrogen bond in an amount of 2,000 ppm by weight or less, more advantageously 1,200 ppm by weight or less, in terms of the amount of nitric acid, based on the total weight of the succinic, glutaric and adipic acids. In the present invention, the term "impurity component having an oxygen-nitrogen bond" is used to indicate organic compounds having a functional group (such as —$NO_2$, —NH—$NO_2$ or =N—OH) having an oxygen-nitrogen bond, and nitrogen oxide type inorganic compounds (such as nitrous acid) excluding nitric acid.

The amount of the impurity component having an oxygen-nitrogen bond contained in the dicarboxylic acid mixture is obtained as follows. NaOH is added to an aqueous solution of the dicarboxylic acid mixture (containing both the originally present nitric acid and the impurity component having an oxygen-nitrogen bond), followed by heating. From the resultant mixture are removed volatile components, such as ammonia. Then, the resultant mixture is subjected to a reduction treatment with Devarda's alloy, and the amount of ammonia produced in the reduction treatment is determined. The determined amount of ammonia produced is expressed in terms of the weight of nitric acid. The obtained weight of nitric acid corresponds to the total of the weight of the nitric acid which has been originally present in the dicarboxylic acid mixture and the weight of the nitric acid which corresponds to the amount of the ammonia produced from the impurity compounds (except the nitric acid) having an oxygen-nitrogen bond.

From the thus obtained total weight (in terms of the weight of nitric acid) of compounds having an oxygen-nitrogen bond (including both the originally present nitric acid and the impurity component having an oxygen-nitrogen bond) is subtracted a separately measured weight of the nitric acid which has been originally present in the dicarboxylic acid mixture to obtain the amount (in terms of the weight of nitric acid) of the impurity component having an oxygen-nitrogen bond (which does not include nitric acid). Some of the compounds as the impurity component having an oxygen-nitrogen bond exhibit an absorbance at a wavelength of 355 nm. The impurities, such as the impurity component having an oxygen-nitrogen bond, are considered to be by-produced by the oxidation reaction with nitric acid in the adipic acid production process. It is most preferred that the impurity component having an oxygen-nitrogen bond is completely removed from the aqueous by-product solution; however, it is not practical to completely remove the impurity component having an oxygen-nitrogen bond, since, in order to completely remove the impurity component having an oxygen-nitrogen bond, it is necessary to repeatedly conduct a treatment with an activated carbon, which is very cumbersome. In a treatment generally conducted, the amount of the impurity component having an oxygen-nitrogen bond contained in the dicarboxylic acid mixture cannot be reduced to a level of lower than about 50 ppm in terms of the amount of nitric acid, based on the total weight of the succinic, glutaric and adipic acids.

The compound having an oxygen-nitrogen bond can be removed from the aqueous by-product solution by the method as used for denitration. Specifically, the compound can be removed by a method in which the aqueous by-product solution is heated at a temperature of from 80 to 200° C. under atmospheric pressure to a reduced pressure of about 80 kPa. Alternatively, the compound can be removed by a method in which the aqueous by-product solution is subjected to a reduction treatment in the presence of a reduction catalyst containing an active metal species comprising at least one metal selected from the group consisting of metals of Groups 7 to 10 of the Periodic Table. The present inventors made studies with respect to a method for removing the impurity component having an oxygen-nitrogen bond, especially an organic compound having a functional group containing an oxygen-nitrogen bond. As a result, it has been found that it is effective to use a method in which the aqueous by-product solution is contacted with an activated carbon. As a specific example of such a removal method, there can be mentioned the above-mentioned method for removing the impurity exhibiting an absorbance at a wavelength of 355 nm.

In the present invention, the dicarboxylic acid mixture used as the raw material for the diol mixture has a nitric acid content of 3% by weight or less, based on the total weight of the dicarboxylic acids contained in the dicarboxylic acid mixture. It is preferred that the dicarboxylic acid mixture does not contain impurities, such as copper values, vanadium values, sulfur values, the tinting substances (e.g., the above-mentioned impurity component having an oxygen-nitrogen bond), which are likely to adversely affect the hydrogenation reaction of the dicarboxylic acid mixture. A dicarboxylic acid mixture containing no such impurities can be obtained by using an appropriate combination of the above-mentioned methods for removing impurities.

Hereinbelow, an explanation is made with respect to preferred combinations of steps for removing impurities from the aqueous by-product solution to thereby obtain a desirable dicarboxylic acid mixture. First, specific examples of preferred purification processes for obtaining a desirable dicarboxylic acid mixture from the aqueous by-product solution are enumerated below.

First purification process: the first purification process comprises the steps of:
(a) heating the aqueous by-product solution at a temperature of from 80 to 200° C. under atmospheric or lower pressure to effect dehydration and denitration of the aqueous by-product solution to obtain a dehydrated and denitrated dicarboxylic acid mixture;
(b) adding water to the obtained dehydrated and denitrated dicarboxylic acid mixture to thereby obtain an aqueous denitrated dicarboxylic acid mixture solution; and
(c) contacting the aqueous denitrated dicarboxylic acid mixture solution with a cation exchange resin to thereby remove copper values and vanadium values.

Second purification process: the second purification process comprises the steps of:
(a) heating the aqueous by-product solution at a temperature of from 80 to 130° C. under atmospheric or lower pressure, followed by heating at a temperature of from higher than 130° C. to 180° C. under atmospheric pressure, to thereby obtain a dehydrated and denitrated dicarboxylic acid mixture;
(b) adding water to the obtained dehydrated and denitrated dicarboxylic acid mixture to thereby obtain an aqueous denitrated dicarboxylic acid mixture solution;
(c) contacting the aqueous denitrated dicarboxylic acid mixture solution with a cation exchange resin to thereby remove copper values and vanadium values;
(d) heating the resultant aqueous denitrated dicarboxylic acid mixture solution under atmospheric or lower pressure at a temperature sufficient to distill off water from the resultant aqueous denitrated dicarboxylic acid mixture solution and obtain a denitrated dicarboxylic acid mixture;
(e) adding a $C_6$–$C_{14}$ aromatic hydrocarbon having a boiling point of 200° C. or less under atmospheric pressure to the denitrated dicarboxylic acid mixture obtained in step (d), and heating the resultant mixture at a temperature which is not higher than the boiling point of the aromatic hydrocarbon, followed by cooling; and
(f) recovering the denitrated dicarboxylic acid mixture from the mixture obtained in step (e) by filtration, thereby preparing the dicarboxylic acid mixture.

Third purification process: the third purification process comprises contacting the aqueous by-product solution with hydrogen gas in the presence of a reduction catalyst containing an active metal species comprising at least one metal selected from the group consisting of metals of Groups 7 to 10 of the Periodic Table, to thereby reduce nitric acid and the above-mentioned impurity component having an oxygen-nitrogen bond contained in the aqueous by-product solution, thereby obtaining the dicarboxylic acid mixture in the form of an aqueous solution thereof.

Hereinbelow, general explanations are made with respect to the purification processes for obtaining the dicarboxylic acid mixture.

In the purification processes for obtaining the dicarboxylic acid mixture used in the method of the present invention, it is preferred that the denitration of the aqueous by-product solution is conducted in the beginning of the purification process, as in the case of the above-mentioned first to third purification processes. As a preferred example of methods for denitrating the aqueous by-product solution, there can be mentioned a method in which the aqueous by-product solution is heated at a temperature of from 80 to 200° C. under atmospheric or lower pressure. Specifically, this method comprises heating the aqueous by-product solution at a temperature of from 80 to 130° C. under atmospheric or lower pressure for about 10 minutes to about 3 hours, followed by heating at a temperature of from higher than 130° C. to 180° C. under atmospheric pressure for about 1 minute to about 1 hour. As another preferred example of methods for denitrating the aqueous by-product solution, there can be mentioned a method which comprises contacting the aqueous by-product solution with hydrogen gas in the presence of a reduction catalyst containing an active metal species comprising at least one metal selected from the group consisting of metals of Groups 7 to 10 of the Periodic Table, to thereby reduce nitric acid and the impurity component having an oxygen-nitrogen bond contained in the aqueous by-product solution. This method is preferred, because the tinting substances, such as the impurity component having an oxygen-nitrogen bond, can also be removed. When the reduction treatment is conducted using a catalyst, it is more preferred that, prior to the reduction treatment, the aqueous by-product solution is partially denitrated by the following method. The aqueous by-product solution is heated under atmospheric or lower pressure, followed by further heating at a temperature of from 130 to 180° C. under atmospheric pressure, to thereby effect a partial denitration of the aqueous by-product solution. To the resultant partially denitrated dicarboxylic acid mixture is added water to thereby obtain an aqueous solution of the partially denitrated dicarboxylic acid mixture. The thus obtained aqueous solution of the partially denitrated dicarboxylic acid mixture is then subjected to a reduction treatment using a catalyst.

When the removal of copper values and vanadium values from the dicarboxylic acid mixture can be conducted by the use of a cation exchange resin as in the case of the above-mentioned first and second purification processes, it is especially preferred to conduct the denitration of the aqueous by-product solution in the beginning of the purification process, since the presence of nitric acid in the dicarboxylic acid mixture causes a lowering of the efficiency of removing copper values and vanadium values by the use of a cation exchange resin.

In the present invention, after the denitration step, it is preferred to remove copper values and vanadium values from the aqueous denitrated dicarboxylic acid mixture solution by the use of a cation exchange resin. Specifically, the removal of copper values and vanadium values is conducted as follows. The aqueous denitrated dicarboxylic acid mixture solution is contacted with a cation exchange resin. When the denitration of the aqueous by-product solution is conducted by heating, the resultant denitrated dicarboxylic acid mixture is obtained in the form of a solid. In such a case, ion-exchanged water is added to the denitrated dicarboxylic acid mixture to thereby obtain a 5 to 50% by weight aqueous solution of the denitrated dicarboxylic acid mixture, and the obtained aqueous denitrated dicarboxylic acid mixture solution is contacted with a cation exchange resin. After the treatment with the cation exchange resin (i.e., the removal of copper values and vanadium values by the use of the cation exchange resin), if desired, the aqueous dicarboxylic acid mixture solution may be subjected to further dehydration and denitration.

By contacting an aqueous solution of the dicarboxylic acid mixture with an anion adsorptive substance, removal of a sulfur compound from the dicarboxylic acid mixture and decoloration of the dicarboxylic acid mixture can be effected, wherein the "decoloration of the dicarboxylic acid mixture" means removal of the tinting substances, such as the impurity component having an oxygen-nitrogen bond, from the dicarboxylic acid mixture. This step for the removal of a sulfur compound and the decoloration may be omitted when the dicarboxylic acid mixture in the course of the purification has a small sulfur content and/or is free from coloration. It is preferred that the treatment of the dicarboxylic acid mixture with an anion adsorptive substance is conducted after the treatment of the dicarboxylic acid mixture with the cation exchange resin. The decoloration achieved by the anion adsorptive substance treatment is larger when the cation exchange resin treatment is conducted prior to the anion adsorptive substance treatment than when the cation exchange resin treatment is conducted after the anion adsorptive substance treatment; however, the reason for this has not yet been elucidated. Further, when the dicarboxylic acid mixture in the course of the purification is subjected to the cation exchange resin treatment using a sulfonic acid type cation exchange resin prior to the anion adsorptive substance treatment, a sulfur compound derived from a sulfonic acid type cation exchange resin can also be removed.

Further, for obtaining a desirable dicarboxylic acid mixture, each of the above-mentioned purification processes may further comprise the step of contacting the aqueous denitrated dicarboxylic acid mixture solution with an activated carbon. This step using an activated carbon may be conducted at any time after the denitration step. By contacting the aqueous denitrated dicarboxylic acid mixture solution with an activated carbon, decoloration of the aqueous dicarboxylic acid mixture solution (i.e., removal of the tinting substances, such as the impurity component having an oxygen-nitrogen bond, from the aqueous dicarboxylic acid mixture solution) can be effected.

As in the case of the above-mentioned second purification process, the purification process may comprise the steps of: adding an aromatic hydrocarbon to the denitrated dicarboxylic acid mixture, heating the resultant mixture, followed by cooling, and recovering the denitrated dicarboxylic acid mixture from the mixture by filtration. These steps are effective for removal of sulfur from the aqueous dicarboxylic acid mixture solution and for decoloration of the aqueous dicarboxylic acid mixture solution. By conducting these steps, it is possible to obtain a dicarboxylic acid mixture having small contents of impurities which are likely to adversely affect the hydrogenation reaction. With respect to the treatment with an aromatic hydrocarbon, this treatment can be conducted after the denitration and the removal of copper values and vanadium values. When the dicarboxylic acid mixture is subjected to treatment using the anion adsorptive substance as well as the treatment using the aromatic hydrocarbon treatment, it is possible to obtain a dicarboxylic acid mixture having very small contents of impurities.

Further examples of methods for effectively removing impurities from the aqueous by-product solution include a distillation conducted by heating under a reduced pressure, and a steam distillation conducted under a reduced pressure. These methods can be conducted in combination with any of the above-mentioned purification processes.

As mentioned above, in the present invention, the purification of the aqueous by-product solution can be conducted by using an appropriate combination of the above-mentioned methods for removing impurities. For almost completely removing impurities from the aqueous by-product solution obtained in the adipic acid production process, it is preferred to subject the aqueous by-product solution to purification. The purification process comprises the following steps ① to ⑤:

① dehydration and denitration by heating (in which the aqueous by-product solution is heated at a temperature of from 100 to 130° C. under atmospheric or lower pressure for about 10 minutes to 3 hours, and then, heated at a temperature of from higher than 130° C. to 180° C. under atmospheric pressure for about 1 minute to about 1 hour);

② removal of copper values and vanadium values using a cation exchange resin;

③ removal of impurities using a liquid anion exchange substance;

④ further removal of impurities using an activated carbon; and

⑤ removal of sulfur values and decolorization using an anion exchange resin.

If desired, step ③ above for removal of impurities using a liquid anion exchange substance may be omitted and, instead, the amount of the activated carbon used in step ④ above may be increased.

In the method of the present invention, the dicarboxylic acid mixture, which is obtained by purifying the by-product solution by any of the above-mentioned purification processes, is subjected to hydrogenation in the presence of water, hydrogen gas and a hydrogenation catalyst containing an active metal species comprising ruthenium and tin, to thereby obtain a hydrogenation reaction mixture comprising a diol mixture comprising 1,4-butanediol, 1,5-pentanediol and 1,6-hexanediol. The hydrogenation catalyst used in the present invention contains an active metal species comprising ruthenium and tin. From the viewpoint of the activity of the hydrogenation catalyst, it is preferred that the active metal species contained in the hydrogenation catalyst further comprises at least one metal selected from the group consisting of metals of Group 7 of the Periodic Table and/or at least one metal selected from the group consisting of metals of Group 8 of the Periodic Table other than ruthenium and metals of Groups 9 and 10 of the Periodic Table. Among the metals of Group 7 of the Periodic Table, rhenium is more preferred, since rhenium exhibits a high activity, and among the metals of Group 8 of the Periodic Table other than ruthenium and metals of Groups 9 and 10 of the Periodic Table, platinum is more preferred, since platinum exhibits a very high activity.

The hydrogenation catalyst used in the present invention may be either a non-carrier-supported catalyst (i.e., catalyst having no carrier) or a carrier-supported catalyst (i.e., catalyst comprising a carrier having carried thereon the active metal species). Examples of carriers used in the carrier-supported catalysts include porous carriers generally used in the art, such as an activated carbon, alumina and silica. Of these porous carriers, from the viewpoint of acid resistance, an activated carbon, titania and zirconia are preferred, and an activated carbon is more preferred. As the activated carbon, either a steam-activated carbon or a chemically activated carbon can be used. The activated carbon may be in a granular form or in a powder form, depending on the type of the hydrogenation reaction. With respect to the method for causing the active metal species to be carried on a carrier, there is no particular limitation, and any of the conventional methods generally used in the production of a carrier-supported catalyst can be employed. Examples of such conventional methods include a dipping method and an ion exchange method. When the dipping method is used, metal sources for the active metal species are dissolved in a solvent (such as water) to thereby prepare a solution of the metal sources, and a porous carrier which has been separately prepared is dipped in the solution to thereby cause the metal species to be carried on the carrier. With respect to the order of causing metals to be carried on the carrier as the active metal species, there is no particular limitation. All of the metals as the active metal species may be simultaneously caused to be carried on the carrier. Alternatively, the metals as the active metal species may be separately caused to be carried on the carrier. Further, if desired, each of the metals as the active metal species may be stepwise caused to be carried on the carrier.

The types of metal sources for the active metal species used in the production of the catalyst may vary depending on the method for producing the catalyst. Representative examples of metal sources include an inorganic acid salt, such as a nitrate, a sulfate or a chloride; an organic acid salt, such as an acetate; a hydroxide; an oxide; and an organometallic compound, such as an amine complex or a carbonyl complex. Preferred examples of sources for ruthenium include ruthenium chloride, ruthenium bromide, ruthenium nitrate, acetylacetonatoruthenium, ruthenium carbonyl, Ruthenium Black, a ruthenium powder, ruthenium oxide, ruthenium nitrosyl nitrate and ammonium oxydecachlorodiruthenate. Examples of sources for tin include tin(II) chloride, sodium stannate and tin(II) acetate. Examples of sources for rhenium include dirhenium decacarbonyl (rhenium carbonyl), rhenium oxide, perrhenic acid, ammonium perrhenate, rhenium chloride and cyclopentadienylrhenium tricarbonyl. Examples of sources for platinum include chloroplatinic acid, platinum nitrate, acetylacetonatoplatinum, platinum chloride, platinum bromide and platinum cyanide.

In the present invention, each of the amounts of ruthenium and tin carried on the carrier is independently from 0.5 to 50% by weight, preferably from 1 to 10% by weight, based on the weight of the carrier. It is preferred that the atomic ratio of ruthenium to tin (ruthenium:tin) is from 1:0.1 to 1:2, more advantageously from 1:0.2 to 1:1.3. With respect to the above-mentioned metal selected from the group consisting of metals of Group 7 of the Periodic Table and/or the above-mentioned metal selected from the group consisting of metals of Group 8 of the Periodic Table other than ruthenium and the above-mentioned metals of Groups 9 and 10 of the Periodic Table (these metals are hereinafter, collectively, referred to as the "optional metal"), the amount of the optional metal (wherein, when a plurality of optional metals are selected, the amount means the total amount of the plurality of optional metals) is preferably from 0.01 to 5, more preferably from 0.1 to 2, in terms of the atomic ratio of the optional metal to ruthenium.

The carrier having carried thereon the metal species is subjected to drying, followed by reduction treatment, to thereby obtain the hydrogenation catalyst used in the present invention. If desired, after the drying and before the reduction treatment, the carrier having carried thereon the metal species may be calcined. The drying of the carrier having carried thereon the metal species is performed under a reduced pressure or under a stream of a dry gas (such as dry nitrogen gas or dry air), usually at a temperature of from room temperature to less than 200° C. The calcination of the dried carrier having carried thereon the active metal species is generally conducted at a temperature of from 200 to 600° C. for 1 to 24 hours under a stream of nitrogen, air or the like. The reduction treatment of the carrier having carried thereon the metal species can be conducted either in a liquid phase or in a gaseous phase. The gaseous phase reduction is generally conducted at a temperature of from 200 to 500° C. for 30 minutes to 24 hours using hydrogen gas as a reduction gas.

With respect to the non-carrier-supported hydrogenation catalyst used in the present invention, an explanation is made below. The non-carrier-supported hydrogenation catalyst can be prepared either by a method in which an aqueous solution of metal sources for the active metal species is reduced using a reducing agent, or by a method in which solids containing the active metal species are reduced in a liquid phase or in a gaseous phase, wherein the solids are obtained by coprecipitation. The non-carrier-supported hydrogenation catalyst can be prepared using the metal sources mentioned above in connection the carrier-supported hydrogenation catalyst. It is preferred that the atomic ratio of ruthenium to tin (ruthenium:tin) is from 1:0.1 to 1:2, more advantageously from 1:0.2 to 1:1.3. With respect to the optional metal selected from the group consisting of metals of Group 7 of the Periodic Table and/or the optional metal selected from the group consisting of metals of Group 8 of the Periodic Table other than ruthenium and metals of Groups 9 and 10 of the Periodic Table, the amount of the optional metal (wherein, when a plurality of optional metals are selected, the amount means the total amount of the plurality of optional metals) is preferably from 0.01 to 5, more preferably from 0.1 to 2, in terms of the atomic ratio of the optional metal to ruthenium.

In the present invention, a dicarboxylic acid mixture comprising succinic acid, glutaric acid and adipic acid and having a nitric acid content of 3% by weight or less, based on the total weight of the succinic, glutaric and adipic acids, is subjected to hydrogenation in the presence of water, hydrogen gas and a hydrogenation catalyst containing an active metal species comprising ruthenium and tin. As already described above, it is preferred that the active metal species contained in the hydrogenation catalyst further comprises at least one optional metal selected from the group consisting of metals of Group 7 of the Periodic Table and/or at least one optional metal selected from the group consisting of metals of Group 8 of the Periodic Table other than ruthenium and metals of Groups 9 and 10 of the Periodic Table. If desired, a solvent (such as an alcohol or an ether) other than water may be added to the hydrogenation reaction system. It is preferred that the water in the hydrogenation reaction system is present in an amount such that the water can dissolve therein all of the dicarboxylic acid mixture at the hydrogenation reaction temperature. Specifically, the amount of the water is generally from 0.3 to 100 parts by weight, preferably from 1 to 20 parts by weight, more preferably from 2 to 10 parts by weight, per part by weight of the dicarboxylic acid mixture.

The hydrogenation reaction temperature is preferably from 100 to 300° C., more preferably from 130 to 270° C. The hydrogenation reaction pressure is preferably from 1 to 25 MPa, more preferably from 5 to 20 MPa. The amount of the hydrogenation catalyst is preferably from 0.001 to 10 parts by weight, more preferably from 0.01 to 1 part by weight, per part by weight of the dicarboxylic acid mixture.

The hydrogenation reaction can be conducted either in a continuous manner or in a batchwise manner. Further, the hydrogenation reaction may be either a suspension reaction conducted in a liquid phase or a fixed-bed flow reaction.

By the above-mentioned method, a hydrogenation reaction mixture comprising a diol mixture comprising 1,4- butanediol, 1,5-pentanediol and 1,6-hexanediol can be obtained. The diols obtained by the method of the present invention are useful as raw materials for polyester resins, urethane foams, urethane coating materials, adhesives and the like. For example, with respect to the use of the diols as a raw material for a polyurethane, the diols as such can be used as chain extenders for forming a polyurethane. Further, the diols can also be used for forming soft segments of a polyurethane by converting the diols into polycarbonate diols or polyester diols.

In the present invention, 1,4-butanediol, 1,5-pentanediol and 1,6-hexanediol can be recovered from the obtained hydrogenation reaction mixture comprising the diol mixture. With respect to the method for recovering these diols, there is no particular limitation. For example, 1,4-butanediol and a mixture of 1,5-pentanediol and 1,6-hexanediol can be separately recovered from the diol mixture by a method comprising:

(i) adjusting the temperature of the hydrogenation reaction mixture comprising the diol mixture to a temperature of from room temperature to less than 100° C., followed by a gas-liquid separation under atmospheric or lower pressure under which water is not boiled at the adjusted temperature of the mixture to remove the hydrogen gas from the hydrogenation reaction mixture;

(ii) heating the hydrogen gas-removed hydrogenation reaction mixture under atmospheric pressure to thereby distill off the water and a mixture of cyclic ethers and monohydric alcohols which are by-produced in the hydrogenation reaction;

(iii) subjecting the resultant mixture to multi-stage distillation to distill off the water and γ-butyrolactone by-produced in the hydrogenation reaction, thereby obtaining a purified diol mixture;

(iv) subjecting the purified diol mixture to multi-stage distillation to obtain 1,4-butanediol as a low boiling point component while withdrawing a high boiling point mixture; and (v) subjecting the high boiling point mixture withdrawn in step (iv) to multi-stage distillation to obtain a mixture of 1,5-pentanediol and 1,6-hexanediol as a distillate.

In step (i) of this method, the hydrogenation reaction mixture comprising the diol mixture, which is obtained by the above-mentioned hydrogenation reaction, is subjected to gas-liquid separation to remove the hydrogen gas from the hydrogenation reaction mixture. Specifically, the gas-liquid separation is conducted as follows. The hydrogenation reaction mixture comprising the diol mixture is cooled to a temperature of from room temperature to less than 100° C. Then, the pressure is lowered to atmospheric pressure or lower pressure under which water is not boiled at the temperature of the cooled mixture, thereby removing an excess amount of hydrogen gas (remaining after the hydrogenation reaction) from the hydrogenation reaction mixture comprising the diol mixture. The removed hydrogen gas can be recycled to the hydrogenation reaction system after removing carbon monoxide and carbon dioxide (which are present in very small amounts in the hydrogen gas) from the hydrogen gas by using a removing apparatus.

In step (ii) of the above-mentioned method, the hydrogen gas-removed hydrogenation reaction mixture is then heated to 100 to 120° C. under atmospheric pressure to thereby distill off most of the water and a mixture of cyclic ethers (e.g., tetrahydrofuran, tetrahydropyran and hexamethylene oxide) and monohydric alcohols (e.g., propanol, butanol, pentanol and hexanol) which are by-produced in the hydrogenation reaction.

In step (iii) of the above-mentioned method, the resultant mixture, from which most of water and the above-mentioned cyclic ethers/monohydric alcohols mixture (having a low boiling point) have been removed, is then subjected to multi-stage distillation to distill off the remaining water and γ-butyrolactone by-produced in the hydrogenation reaction, thereby obtaining a purified diol mixture, wherein the multi-stage distillation is conducted using a multi-stage distillation column having 5 to 15 stages under conditions wherein the column bottom temperature is from 130 to 190° C., the column bottom pressure is from 5.5 to 7.0 kPa, the column top temperature is from 10 to 60° C., and the column top pressure is from 3.5 to 5.5 kPa. By the multi-stage distillation, very small amounts of pentanol, hexanol and the like are distilled off, together with γ-butyrolactone.

In step (iv) of the above-mentioned method, the purified diol mixture is subjected to multi-stage distillation to obtain 1,4-butanediol as a low boiling point component while withdrawing a high boiling point mixture. The multi-stage distillation for obtaining 1,4-butanediol can be conducted, for example, by using a multi-stage distillation column having 20 to 40 stages under conditions wherein the column bottom temperature is from 140 to 180° C., the column bottom pressure is from 4.0 to 7 kPa, the column top temperature is from 30 to 60° C., the column top pressure is from 0.3 to 1.0 kPa, and the purified diol mixture is fed to a middle stage (i.e., the fifteenth stage from the bottom or around this numbered stage) of the multi-stage distillation column. The high boiling point mixture is withdrawn from the bottom of the column.

In step (v) of the above-mentioned method, by the above operation, the high boiling point mixture withdrawn in step (iv) above is subjected to multi-stage distillation to obtain a mixture of 1,5-pentanediol and 1,6-hexanediol as a distillate. Specifically, the multi-stage distillation for obtaining a mixture of 1,5-pentanediol and 1,6-hexanediol can be conducted, for example, by using a multi-stage distillation column having 3 to 15 stages under conditions wherein the column bottom temperature is from 180 to 220° C., the column bottom pressure is from 5.5 to 9.0 kPa, the column top temperature is from 140 to 180° C., the column top pressure is from 4.0 to 7.0 kPa, and the purified diol mixture from which 1,4-butanediol has been separated is fed to the middle stage of the multi-stage distillation column.

Each of the above-mentioned distillation operations can be conducted either in a continuous manner or in a batchwise manner.

With respect to the 1,4-butanediol obtained by the above-mentioned method, it is preferred that the 1,4-butanediol has a purity of 98.5% or more, and the total amount of lactones, hydroxycarboxylic acids, monohydric alcohols and diols having a secondary OH group and a primary OH group, which are impurities contained in the 1,4-butanediol, is less than 0.5% by weight, wherein the term "secondary OH group" means a hydroxyl group directly bonded to a secondary carbon atom and the term "primary OH group" means a hydroxyl group directly bonded to a primary carbon atom. Examples of the above-mentioned "lactones" include γ-butyrolactone, δ-valerolactone and ε-caprolactone; examples of the above-mentioned "hydroxycarboxylic acids" include hydroxybutylic acid, hydroxyvaleric acid and hydroxycaproic acid; examples of the above-mentioned "monohydric alcohols" include, as mentioned above, propanol, butanol, pentanol and hexanol; and examples of the above-mentioned "diols having a secondary OH group and a primary OH group" include 1,3-butanediol, 1,4-pentanediol and 1,5-hexanediol.

Each of δ-valerolactone and ε-caprolactone, which are impurities, has a boiling point close to that of 1,4-butanediol. Therefore, for separating δ-valerolactone and ε-caprolactone from 1,4-butanediol by distillation, it is necessary to use a multi-stage distillation column having a large number of stages, so that equipment for distillation becomes disadvantageously large. For this reason, it is preferred that the amounts of δ-valerolactone and ε-caprolactone are as small as possible. Illustratively stated, since these lactones are produced as intermediates in the hydrogenation reaction of the dicarboxylic acids, it is preferred that the conditions for the hydrogenation reaction is selected such that the total amount of δ-valerolactone and ε-caprolactone becomes less than 0.5% by weight, based on the weight of 1,4-butanediol produced. However, when large amounts of δ-valerolactone and ε-caprolactone are by-produced in the hydrogenation reaction due to the limited ability of an apparatus used, that is, when the total amount of δ-valerolactone and ε-caprolactone is 0.5% by weight or more, based on the weight of 1,4-butanediol produced, the lactones can be removed by the following method. To the hydrogenation reaction mixture comprising the diol mixture (after the gas-liquid separation or after the distillation which is conducted immediately after the gas-liquid separation) is added at least one compound selected from the group of consisting of a hydroxide, carbonate and hydrogencarbonate of an alkali metal, and a hydroxide, carbonate, and hydrogencarbonate of an alkaline earth metal, wherein the amount of the compound is from 0.01 to 10% by weight, based on the weight of the hydrogenation reaction mixture, to thereby convert lactones and hydroxycarboxylic acids contained in the hydrogenation reaction mixture into alkali metal salts and/or alkaline earth metal salts, which have a boiling point higher than those of the diols. Such metal salts having a boiling point higher than those of the diols can be easily removed.

When the 1,4-butanediol obtained by the method of the present invention is used as a raw material for a polyurethane, it is preferred that the total amount of lactones, hydroxycarboxylic acids, monohydric alcohols and diols having a secondary OH group and a primary OH group, which are contained as impurities in the 1,4-butanediol, is 0.5% by weight or less. When the total amount of these impurities is more than 0.5% by weight, the polymerization reactivity of the 1,4-butanediol becomes disadvantageously low, so that it becomes difficult to obtain a high molecular weight polyurethane. Further, the presence of a lactone and/or a hydroxycarboxylic acid in a polyurethane adversely affects the properties (such as hydrolysis resistance) of the polyurethane.

The mixture of 1,5-pentanediol and 1,6-hexanediol obtained by the above-mentioned method contains 1,5-pentanediol as a main component. The present inventors have analyzed the impurities contained in the mixture. As a result, it has been found that the mixture contains substantially no 1,5-hexanediol and substantially no 1,4-dihydroxycyclohexane, which are necessarily contained as impurities in 1,5-pentanediol produced by any of the conventional processes. Specifically, the mixture of 1,5-pentanediol and 1,6-hexanediol obtained in the present invention has a 1,5-hexanediol content of only 0.1% by weight or less and 1,4-dihydroxycyclohexane content of only 0.1% by weight or less, whereas 1,5-pentanediol produced by the conventional process has a 1,5-hexanediol content of 0.2% by weight or more and a 1,4-dihydroxycyclohexane content of 0.2% by weight or more.

Conventionally, 1,5-pentanediol is produced using as a raw material a carboxylic acid mixture containing glutaric acid, adipic acid and 6-hydroxycaproic acid which are by-produced in the production of cyclohexanone and/or cyclohexanol by air oxidation of cyclohexane. Specifically, 1,5-pentanediol is conventionally produced by a method comprising esterifying a carboxylic acid mixture containing glutaric acid, adipic acid and 6-hydroxycaproic acid, hydrogenating the resultant mixture in the presence of a copper-containing catalyst to thereby obtain 1,5-pentanediol and 1,6-hexanediol, and separating the obtained 1,5-pentanediol from the obtained 1,6-hexanediol by distillation (see U.S. Pat. No. 3,268,588). However, the 1,5-pentanediol obtained by this conventional method has a 1,5-hexanediol content as large as from 0.2 to 1% by weight and a 1,4-dihydroxycyclohexane content as large as from 0.2 to 1% by weight. 1,5-hexanediol is a diol having a secondary OH group and a primary OH group. When the conventional 1,5-pentanediol containing 1,5-hexanediol is used as a raw material for producing a polycarbonate diol or a polyester polyol, the secondary OH group of the 1,5-hexanediol forms a terminal group of the produced polyol (i.e., the polycarbonate diol or the polyester polyol), since the secondary OH group has a low reactivity. Therefore, when the polyol is subjected to urethanation, disadvantages are likely to occur wherein the polymerization rate is low and the molecular weight of the obtained polyurethane is not satisfactorily high. Further, when the conventional 1,5-pentanediol (containing 1,5-hexanediol) as such is used as a chain extender for producing a polyurethane, substantially the same disadvantages as mentioned above are likely to occur. With respect to 1,4-dihydroxycyclohexane, both of the two OH groups thereof are secondary OH groups, which have a low reactivity. Therefore, 1,4-dihydroxycyclohexane has a problem in that 1,4-dihydroxycyclohexane remaining unreacted is likely to be contained in the polycarbonate diol.

On the other hand, the mixture of 1,5-pentanediol and 1,6-hexanediol obtained by the method of the present invention contains substantially no 1,5-hexanediol and substantially no 1,4-dihydroxycyclohexane. Therefore, the mixture of 1,5-pentanediol and 1,6-hexanediol can be advantageously used not only as a chain extender for producing a polyurethane, but also as raw materials for a polycarbonate diol and a polyester polyol, which are used to form soft segments of a polyurethane. Especially, a carbonate diol copolymer (see Examined Japanese Patent Application Publication No. 5-029648) obtained by copolymerizing 1,5-pentanediol with 1,6-hexanediol in the presence of ethylene carbonate has recently drawn attention, because a thermoplastic polyurethane (see Examined Japanese Patent Application Publication No. 7-684) which is produced using the carbonate diol copolymer as a raw material has not only an excellent hydrolysis resistance and an excellent heat resistance but also a greatly improved low temperature flexibility, as compared to those of a thermoplastic polyurethane produced using a polycarbonate diol obtained by polymerizing only 1,6-hexanediol in the presence of ethylene carbonate. Accordingly, the mixture of 1,5-pentanediol and 1,6-hexanediol obtained by the method of the present invention can be advantageously used as a raw material for a carbonate diol copolymer.

BEST MODE FOR CARRYING OUT THE INVENTION

Hereinbelow, the present invention will be described in more detail with reference to the following Reference Examples, Examples and Comparative Examples; however, they should not be construed as limiting the scope of the present invention.

In the following Examples and Comparative Examples, various properties of an aqueous by-product solution, a dicarboxylic acid mixture and a diol mixture were measured by the following methods.

(1) Concentrations of Succinic Acid, Glutaric Acid and Adipic Acid

To 100 parts by weight of an aqueous dicarboxylic acid mixture solution or an aqueous by-product solution were added 10 parts by weight of pimelic acid as an internal standard, thereby obtaining a sample solution. The sample solution was analyzed by high performance liquid chromatography (HPLC) under the below-mentioned analysis conditions to determine the individual concentrations of succinic acid, glutaric acid and adipic acid.

Also, from the results of the analysis, the total weight of succinic acid, glutaric acid and adipic acid was calculated, and the calculated total weight of the dicarboxylic acids was used in the below-described determinations of the contents of nitric acid, copper, vanadium, sulfur and the above-defined impurity component having oxygen-nitrogen bond, which were contained in the dicarboxylic acid mixture.

Conditions for HPLC

HPLC apparatus: High performance liquid chromatograph Model LC-6A (manufactured and sold by Shimadzu Corporation, Japan)

Column: SCR-101H (manufactured and sold by Shimadzu Corporation, Japan)

Column temperature: 40° C.

Moving phase: aqueous perchloric acid solution (pH 2.3)

Flow rate: 0.8 ml/min

Amount of sample injection: 5 µl

Detector: differential refractometer (2) Nitric Acid Content

To a dicarboxylic acid mixture was added ion-exchanged water, thereby obtaining a sample solution having a dicarboxylic acid mixture content of 2% by weight (also in the case of the measurement of the nitric acid content of an aqueous by-product solution, the dicarboxylic acid mixture content of the by-product solution was adjusted to obtain a sample solution having a dicarboxylic acid mixture content of 2% by weight). This sample solution was analyzed by high performance liquid chromatography (HPLC) under the below-mentioned analysis conditions. From the results of the analysis, the nitric acid content, based on the total weight of succinic acid, glutaric acid and adipic acid, was determined.

Conditions for HPLC

HPLC apparatus: High performance liquid chromatograph Model LC-6A (manufactured and sold by Shimadzu Corporation, Japan)

Column: TSK-GEL GL-DEAE-2SW (manufactured and sold by Tosoh Corp., Japan)

Column temperature: 40° C.

Moving phase: a liquid prepared by adding 85% phosphoric acid to an acetonitrile/water mixture having an acetonitrile/water volume ratio of 30/70 so that the phosphoric acid concentration of the resultant solution became 0.085 mol/l, followed by adjustment of pH to 3.4 with aqueous ammonia Flow rate: 0.8 ml/min Amount of sample injection: 50 µl Detector: UV detector (210 nm)

(3) Copper, Vanadium and Sulfur Contents

To a dicarboxylic acid mixture was added ion-exchanged water, thereby obtaining a sample solution having a dicarboxylic acid mixture content of 10% by weight (also in the case of the measurement of the copper, vanadium and sulfur contents of an aqueous by-product solution, the dicarboxylic acid mixture content of the by-product solution was adjusted to obtain a sample solution having a dicarboxylic acid mixture content of 10% by weight). This sample solution was analyzed by an inductively coupled plasma emission analyzer (ICP) (manufactured and sold by JOBIN YVON EMISSION Instrument S. A., U.S.A.). From the results of the analysis, the copper, vanadium and sulfur contents, each based on the total weight of succinic acid, glutaric acid and adipic acid, were individually determined.

(4) Absorption Coefficient as Measured at 355 nm 0.1 g of a solid dicarboxylic acid mixture was dissolved in 10 g of distilled water to obtain a sample solution. Using a spectrophotometer (manufactured and sold by Shimadzu Corporation, Japan) having a 1 cm-long cell, the absorbance of the sample solution at 355 nm was measured at room temperature. When the absorbance of the sample solution was 0.001 or less, another sample solution having a high dicarboxylic acid mixture concentration which is 10 times that of the above-mentioned sample solution was prepared (specifically, another sample solution was prepared by dissolving 1 g of the dicarboxylic acid mixture in 10 g of distilled water), and the measurement of the absorbance was conducted again with respect to this sample solution having a high dicarboxylic acid mixture concentration. Based on the measured absorbance, the absorption coefficient at 355 nm was calculated by the following formula:

$$E = A/(c \times b)$$

wherein E represents the absorption coefficient at 355 nm, A represents the absorbance of the sample solution prepared by dissolving the dicarboxylic acid mixture in distilled water, which is measured at room temperature, c represents the amount (g) of the dicarboxylic acid mixture dissolved in 100 g of distilled water, and b represents the length (cm) of a cell used for measuring the absorbance.

(5) Content of the Impurity Component Having an Oxygen-nitrogen Bond

An aqueous dicarboxylic acid mixture solution having a predetermined concentration of a dicarboxylic acid mixture was prepared. To the prepared aqueous dicarboxylic acid mixture solution was added an approximately 50% aqueous NaOH solution, wherein the volume ratio of the aqueous NaOH solution to the aqueous dicarboxylic acid mixture solution was 1/3 to 1/2, followed by addition of methanol which was used in approximately the same amount as that of the aqueous NaOH solution used. The resultant mixture was heated for about 1 hour to reflux methanol. Then, the methanol was distilled off together with a basic substance. To the resultant aqueous dicarboxylic acid mixture solution was added an appropriate amount of Devarda's alloy, followed by addition of methanol, wherein the volume ratio of the methanol to the aqueous dicarboxylic acid mixture solution was 1/3 to 1/2. The resultant mixture was heated for 1 hour to reflux methanol, followed by distilling off methanol together with ammonia. The amount of ammonia distilled off with methanol was determined as the amount of ammonia formed in the aqueous dicarboxylic acid mixture solution by neutralization titration using diluted hydrochloric acid. The determined amount of ammonia produced was expressed in terms of the weight of nitric acid. The obtained weight of nitric acid corresponds to the total of the weight of the nitric acid which has been originally present in the dicarboxylic acid mixture and the weight of the nitric acid which corresponds to the amount of the ammonia produced from the impurity compounds (except the nitric acid) having an oxygen-nitrogen bond. From the thus obtained total weight (in terms of the weight of nitric acid) of compounds having an oxygen-nitrogen bond (including both the originally present nitric acid and the impurity component having an oxygen-nitrogen bond) was subtracted the weight of the nitric acid which has been originally present in the dicarboxylic acid mixture (wherein the weight of the originally present nitric acid was measured by the above-mentioned method) to obtain the amount (in terms of the weight of nitric acid) of the impurity component having an oxygen-nitrogen bond (which does not include nitric acid), and the content of the impurity component having an oxygen-nitrogen bond in the dicarboxylic acid mixture was calculated as the content, based on the total weight of succinic acid, glutaric acid and adipic acid.

(6) Analysis of a Diol Mixture

A diol mixture was diluted with an appropriate amount of dioxane so that the diol mixture concentration of the resultant diluted diol mixture became approximately 1% by weight. To the diluted diol mixture was added diethylene glycol diethyl ether which was used as an internal standard in an amount wherein the concentration of diethylene glycol diethyl ether in the resultant solution became approximately 1% by weight, thereby obtaining a sample solution. The obtained sample solution was analyzed by gas chromatography (GC) under the below-mentioned analysis conditions to determine 1,4-butanediol, 1,5-pentanediol, 1,6-hexanediol and by-products, which were contained in the diol mixture.

Further, from the results of the analysis, the yields of the diols in the diol mixture, based on the amounts of the corresponding dicarboxylic acids in the dicarboxylic acid mixture used as a raw material, were calculated, respectively.

Conditions for GC
  GC apparatus: gas chromatograph Model GC-14B (manufactured and sold by Shimadzu Corporation, Japan)
  Column: DB-WAX (column length: 30 m, inner diameter: 0.25 mm, film thickness: 0.25 μm) (manufactured and sold by J & W Scientific, U.S.A.)
  Carrier gas: helium
  Detector: flame ionization detector (FID)

Hydrogenation catalysts used in the Examples and the Comparative Examples were prepared in the following Reference Examples 1 and 2.

REFERENCE EXAMPLE 1

Preparation of a Hydrogenation Catalyst (Ru—Sn—Re Catalyst)

7.0 g of ion-exchanged water was charged into a 100 ml eggplant type flask, and then 1.29 g of ruthenium chloride trihydrate, 0.57 g of tin(II) chloride dihydrate and 1.30 g of rhenium heptaoxide were added in this order to and dissolved in the ion-exchanged water in the eggplant type flask. To the resultant solution was added 10.0 g of a particulate activated carbon (the particle diameter: 10 to 20 mesh, the BET specific surface area measured by the nitrogen adsorption method: 1,100 m²/g) and the resultant mixture was allowed to stand still at room temperature for 15 hours. Then, the mixture was subjected to evaporation by using an evaporator to distill off water to thereby obtain a residue. Then, the obtained residue was subjected to drying treatment under a stream of nitrogen gas at 150° C. for 2 hours and then subjected to reduction treatment in a hydrogen atmosphere at 450° C. for 2 hours. The resultant product was then cooled to room temperature in a nitrogen atmosphere and then allowed to stand still in an atmosphere of an (oxygen/nitrogen) gaseous mixture (ratio of oxygen: 0.1% by volume) for 2 hours. By the method described hereinabove, a hydrogenation catalyst was obtained which comprised an activated carbon having carried thereon 5.0% by weight of ruthenium, 3.0% by weight of tin and 5.0% by weight of rhenium.

REFERENCE EXAMPLE 2

Preparation of a Hydrogenation Catalyst (Ru—Sn—Pt Catalyst)

0.93 g of chloroplatinic acid hexahydrate was charged into a 100 ml eggplant type flask, and then 7.0 ml of 5 N hydrochloric acid was charged into the flask, thereby obtaining a solution. Then, 0.95 g of tin(II) chloride dihydrate and 1.55 g of ruthenium trichloride trihydrate were charged in this order into the flask to obtain a solution. To the obtained solution was added 10.0 g of the same activated carbon as used in Reference Example 1, and the flask containing the resultant mixture was shaken at room temperature for 15 hours. Then, the above-mentioned mixture was subjected to evaporation by using an evaporator to distill off water to thereby obtain a residue. Then, the obtained residue was subjected to drying treatment under a stream of nitrogen gas at 150° C. for 2 hours and then subjected to reduction treatment in a hydrogen atmosphere at 450° C. for 2 hours. The resultant product was then cooled to room temperature in a nitrogen atmosphere and then allowed to stand still in an atmosphere of an (oxygen/nitrogen) gaseous mixture (ratio of oxygen: 0.1% by volume) for 2 hours. By the method described hereinabove, a hydrogenation catalyst was obtained which comprised an activated carbon having carried thereon 6.0% by weight of ruthenium, 5.0% by weight of tin and 3.5% by weight of platinum.

EXAMPLE 1

Preparation of an Aqueous By-product Solution

The oxidation of cyclohexanol (which was obtained by purifying a commercially available product by distillation) with nitric acid (guaranteed reagent) was conducted in accordance with the method described in "Jikken Kagaku Koza (Lectures on Chemical Experiment)" first edition, volume 17, page 182, except that an oxidation catalyst comprising, in combination, 2 g of a copper powder and ammonium vanadate was used, thereby obtaining an aqueous reaction mixture comprising succinic acid, glutaric acid and adipic acid. The obtained aqueous reaction mixture was cooled to deposit crystals of the adipic acid, followed by isolation of the deposited crystals, to thereby obtain an aqueous by-product solution from the reaction mixture. The above-described procedure for the synthesis of adipic acid was further repeated 2 times, and all aqueous by-product solutions obtained by 3 runs of the procedure for the synthesis of adipic acid were mixed together. 5,000 g of the resultant aqueous by-product solution was heated at about 120° C. under atmospheric pressure for 1 hour, thereby separating most of the water and the nitric acid from the aqueous by-product solution, to obtain a residue composed of dicarboxylic acids. To the obtained residue composed of dicarboxylic acids was added ion-exchanged water, to thereby obtain an aqueous solution of dicarboxylic acids having a water content of 67% by weight. To the obtained aqueous solution was added 100 g of a styrene polymer type cation exchange resin having a sulfonic acid group as a cation exchange group (trade name: Amberlite IR-120B) (manufactured and sold by ORGANO CORP., Japan), and the resultant mixture was stirred gently at room temperature for 2 hours to cause the cation exchange resin to react with the copper and vanadium which were used as oxidation catalyst, followed by recovering the cation exchange resin by filtration, to thereby remove copper values and vanadium values from the mixture to obtain a purified aqueous by-product solution. The purified aqueous by-product solution had a water content of 67% by weight. The purified aqueous by-product solution was analyzed by HPLC under the above-mentioned analysis conditions. As a result, it was found that the purified aqueous by-product solution was comprised of 7% by weight of succinic acid, 18% by weight of glutaric acid, 5% by weight of adipic acid and 3% by weight of nitric acid (the nitric acid content of the purified aqueous by-product solution was 10% by weight, based on the total weight of succinic acid, glutaric acid and adipic acid). The purified aqueous by-product solution was also analyzed by ICP under the above-mentioned analysis conditions. As a result, it was found that the copper content, vanadium content and sulfur content of the purified aqueous by-product solution were 6 ppm, 2 ppm and 5 ppm, respectively. Further, with respect to the purified aqueous by-product solution, the absorption coefficient was 0.051 as measured at 355 nm and the content of an impurity component having an oxygen-nitrogen bond was 1,147 ppm.

Preparation of a Dicarboxylic Acid Mixture 500 g of the above-mentioned purified aqueous by-product solution was charged into a 1 litter flask and heated at about 120° C. for 1 hour while stirring and then at 170° C. for 15 minutes while stirring to effect dehydration and denitration of the purified aqueous by-product solution. The resultant reaction mixture was cooled to thereby obtain a dicarboxylic acid mixture.

The obtained dicarboxylic acid mixture was analyzed by HPLC under the above-mentioned analysis conditions. As a result, it was found that the dicarboxylic acid mixture was comprised of 23% by weight of succinic acid, 60% by weight of glutaric acid and 17% by weight of adipic acid. Further, with respect to the dicarboxylic acid mixture, the nitric acid content was 0.1% by weight; the copper content, the vanadium content and the sulfur content were 6 ppm, 2 ppm and 5 ppm, respectively; the absorption coefficient was 0.085 as measured at 355 nm; and the content of an impurity component having an oxygen-nitrogen bond was 1,136 ppm.

Production of a Diol Mixture by a Hydrogenation Reaction

Using the dicarboxylic acid mixture obtained above, a diol mixture was produced as follows.

10 g of water, 5.0 g of the dicarboxylic acid mixture and 0.3 g of the Ru—Sn—Re catalyst prepared in Reference Example 1 were charged into a 100 ml autoclave made of Hastelloy, which was equipped with a magnetic induction type stirrer. The atmosphere in the autoclave was replaced by nitrogen at room temperature and, then, pressurized hydrogen gas was introduced into the autoclave to increase the internal pressure thereof to 2 MPa, and the internal temperature of the autoclave was elevated to 180° C. After the internal temperature of the autoclave reached 180° C., pressurized hydrogen gas was further introduced into the autoclave to increase the internal pressure thereof to 15 MPa, and then a hydrogenation reaction was performed under the above-mentioned internal pressure for 18 hours. After completion of the hydrogenation reaction, a hydrogenation reaction mixture containing a diol mixture was taken out from the autoclave, while leaving the catalyst in the autoclave. The diol mixture contained in the hydrogenation reaction mixture was analyzed by gas chromatography under the above-mentioned analysis conditions to determine the yields of the diols. As a result, it was found that the yields of 1,4-butanediol, 1,5-pentanediol and 1,6-hexanediol were 75%, 98% and 96%, respectively.

Into the autoclave containing the catalyst therein were charged 5.0 g of the dicarboxylic acid mixture and 10 g of water, and a hydrogenation reaction was performed under substantially the same conditions as mentioned above to produce a diol mixture. This procedure for the hydrogenation of the dicarboxylic acid mixture was further repeated 6 times (i.e., 7 runs of the hydrogenation were performed). With respect to the catalyst used, the activity maintenance ratio (%) was calculated by the formula: {(total amount of 1,4-butanediol, 1,5-pentanediol and 1,6-hexanediol which were obtained in the 7th run of the hydrogenation)/(total amount of 1,4-butanediol, 1,5-pentanediol and 1,6-hexanediol which were obtained in the 1st run of the hydrogenation)}×100. When the activity maintenance ratio is less than 100%, it means that the catalytic activity is lowered. The results are shown in Table 1.

EXAMPLE 2

Production of a Diol Mixture by a Hydrogenation Reaction 10 g of water, 5.0 g of the dicarboxylic acid mixture prepared in Example 1 and 0.3 g of the Ru—Sn—Pt catalyst prepared in Reference Example 2 were charged into a 100 ml autoclave made of Hastelloy, which was equipped with a magnetic induction type stirrer. The atmosphere in the autoclave was replaced by nitrogen at room temperature and, then, pressurized hydrogen gas was introduced into the autoclave to increase the internal pressure thereof to 2 MPa, and the internal temperature of the autoclave was elevated to 180° C. After the internal temperature of the autoclave reached 180° C., pressurized hydrogen gas was further introduced into the autoclave to increase the internal pressure thereof to 15 MPa, and then a hydrogenation reaction was performed under the above-mentioned internal pressure for 18 hours. After completion of the hydrogenation reaction, a hydrogenation reaction mixture containing a diol mixture was taken out from the autoclave, while leaving the catalyst in the autoclave. The diol mixture contained in the hydrogenation reaction mixture was analyzed by gas chromatography under the above-mentioned analysis conditions.

Into the autoclave containing the catalyst therein were charged 5.0 g of the dicarboxylic acid mixture and 10 g of water, and a hydrogenation reaction was performed under substantially the same conditions as mentioned above to produce a diol mixture. This procedure for the hydrogenation of the dicarboxylic acid mixture was further repeated 6 times (i.e., 7 runs of the hydrogenation were performed). With respect to the catalyst used, the activity maintenance ratio (%) was calculated by the formula described in Example 1. The results are shown in Table 1.

EXAMPLE 3

Preparation of an Aqueous By-product Solution

The oxidation of cyclohexanol with nitric acid was performed in substantially the same manner as in Example 1 to obtain an aqueous reaction mixture comprising succinic acid, glutaric acid and adipic acid. The obtained aqueous reaction mixture was cooled to deposit crystals of the adipic acid, followed by isolation of the deposited crystals, to thereby obtain an aqueous by-product solution.

Preparation of a Dicarboxylic Acid Mixture
(Preparation by the First Purification Process)

5,000 g of the above-mentioned aqueous by-product solution was heated at about 120° C. under atmospheric pressure for 1 hour and then further heated at a temperature of from 170 to 175° C. under atmospheric pressure for 30 minutes while stirring to effect dehydration and denitration of the aqueous by-product solution. The resultant mixture was cooled to thereby obtain a dehydrated and denitrated dicarboxylic acid mixture. To the obtained dehydrated and denitrated dicarboxylic acid mixture was added ion-exchanged water to thereby obtain an aqueous denitrated dicarboxylic acid mixture solution having a water content of 70% by weight. To the obtained aqueous solution was added 10 g of a styrene polymer type cation exchange resin having a sulfonic acid group as a cation exchange group (trade name: Amberlite IR-120B) (manufactured and sold by ORGANO CORP., Japan), and the resultant mixture was stirred gently at room temperature for 2 hours to cause the cation exchange resin to react with the copper and vanadium which were used as oxidation catalyst, followed by recovering the cation exchange resin by filtration, to thereby remove copper values and vanadium values from the mixture to obtain a purified aqueous dicarboxylic acid mixture solution.

The purified aqueous dicarboxylic acid mixture solution had a water content of 70% by weight, and was comprised of 7% by weight of succinic acid, 18% by weight of glutaric acid and 5% by weight of adipic acid. Further, with respect to the purified aqueous dicarboxylic acid mixture solution, the nitric acid content was 0.17% by weight; the copper content, the vanadium content and the sulfur content were 31 ppm, 20 ppm and 3 ppm, respectively; the absorption coefficient was 0.114 as measured at 355 nm; and the content of an impurity component having an oxygen-nitrogen bond was 1,143 ppm.

Production of a Diol Mixture by a Hydrogenation Reaction

A hydrogenation reaction for producing a diol mixture was performed in substantially the same manner as in Example 1, except that the purified aqueous dicarboxylic acid mixture solution obtained above was used instead of the water and the dicarboxylic acid mixture prepared in Example 1. This procedure for the hydrogenation of the dicarboxylic acid mixture was further repeated 6 times (i.e., 7 runs of the hydrogenation were performed). With respect to the catalyst used, the activity maintenance ratio (%) was calculated by the formula described in Example 1. The results are shown in Table 1.

COMPARATIVE EXAMPLE 1

A diol mixture was produced using, as a raw material, the same purified aqueous by-product solution as used in Example 1 for preparing the dicarboxylic acid mixture. As described in Example 1, the purified aqueous by-product solution had a water content of 67% by weight, and was comprised of 7% by weight of succinic acid, 18% by weight of glutaric acid, 5% by weight of adipic acid and 3% by weight of nitric acid (the nitric acid content of the aqueous by-product solution was 10% by weight, based on the total weight of succinic acid, glutaric acid and adipic acid). Further, with respect to the purified aqueous by-product solution, the copper content, the vanadium content and the sulfur content were 6 ppm, 2 ppm and 5 ppm, respectively; the absorption coefficient was 0.051 as measured at 355 nm; and the content of an impurity component having an oxygen-nitrogen bond was 1,147 ppm. Specifically, the production of a diol mixture was conducted as follows.

Production of a Diol Mixture by a Hydrogenation Reaction

A hydrogenation reaction for producing a diol mixture was performed in substantially the same manner as in. Example 1, except that 15.0 g of the purified aqueous by-product solution mentioned above was used instead of the water and the dicarboxylic acid mixture prepared in Example 1. After completion of the hydrogenation reaction, a hydrogenation reaction mixture containing a diol mixture was taken out from the autoclave, while leaving the catalyst in the autoclave. The diol mixture contained in the hydrogenation reaction mixture was analyzed by gas chromatography under the above-mentioned analysis conditions to determine the yields of the diols. As a result, it was found that the yields of 1,4-butanediol, 1,5-pentanediol and 1,6-hexanediol were 45%, 73% and 72%, respectively.

The above-mentioned procedure for the hydrogenation of the dicarboxylic acid mixture (contained in the purified aqueous by-product solution) was further repeated 6 times (i.e., 7 runs of the hydrogenation were performed). With respect to the catalyst used, the activity maintenance ratio (%) was calculated by the formula described in Example 1. The results are shown in Table 1 together with the results obtained in Examples 1, 2 and 3.

TABLE 1

|  | Activity maintenance ratio (%) |
|---|---|
| Example 1 | 98 |
| Example 2 | 99 |
| Example 3 | 85 |
| Comparative Example 1 | 42 |

As clearly shown in Table 1, in Comparative Example 1 in which the diol mixture is produced using a dicarboxylic acid mixture having a nitric acid content of more than 3% by weight, based on the total weight of succinic acid, glutaric acid and adipic acid, the activity maintenance ratio of the hydrogenation catalyst is disadvantageously low.

EXAMPLE 4

Preparation of a Dicarboxylic Acid Mixture
(Preparation by the First Purification Process)

A dicarboxylic acid mixture was prepared using an aqueous by-product solution obtained in an adipic acid production process, from which adipic acid had been isolated. The aqueous by-product solution was comprised of 55% by weight of water, 19% by weight of glutaric acid, 7% by weight of succinic acid, 11% by weight of adipic acid and 6% by weight of nitric acid. Further, with respect to the aqueous by-product solution, the copper content, the vanadium content and the sulfur content were 0.6% by weight, 0.4% by weight and 340 ppm, respectively; the absorption coefficient was 1.460 as measured at 355 nm: and the content of an impurity component having an oxygen-nitrogen bond was 7,300 ppm. Specifically, the production of a diol mixture was conducted as follows.

1,000 g of the above-mentioned aqueous by-product solution was charged into a beaker and heated at about 120° C. under atmospheric pressure for 1 hour while stirring and, then, at a temperature of from 170 to 175° C. under atmospheric pressure for 30 minutes while stirring to effect dehydration and denitration of the aqueous by-product solution. The resultant mixture was cooled to thereby obtain 380 g of a dehydrated and denitrated dicarboxylic acid mixture. To the obtained, dehydrated and denitrated dicarboxylic acid mixture was added ion-exchanged water to thereby obtain an aqueous denitrated dicarboxylic acid mixture solution having a dicarboxylic acid mixture content of 38% by weight. Then, an insoluble matter was removed from the aqueous denitrated dicarboxylic acid mixture solution by filtration to obtain a filtrate. To the obtained filtrate was added 300 g of a styrene polymer type cation exchange resin having a sulfonic acid group as a cation exchange group (trade name: Amberlite IR-120B) (manufactured and sold by ORGANO CORP., Japan), and the resultant mixture was stirred gently at room temperature for 3 hours to cause the cation exchange resin to react with the copper and vanadium which were used as oxidation catalyst, followed by recovering the cation exchange resin by filtration, to thereby remove copper values and vanadium values from the mixture to obtain a filtrate. To the obtained filtrate was added 300 g of a styrene polymer type anion exchange resin having a quaternary ammonium salt as an anion exchange group (trade name: Amberlite IRA-900) (manufactured and sold by ORGANO CORP., Japan), and the resultant mixture was stirred gently at room temperature for 3 hours to cause the anion exchange resin to react with sulfur values, followed by recovering the anion exchange resin by filtration, to thereby remove the sulfur values from the mixture to obtain a dicarboxylic acid mixture in the form of a purified aqueous solution thereof.

The thus obtained purified aqueous dicarboxylic acid mixture solution was analyzed by HPLC under the above-mentioned analysis conditions. As a result, it was found that the concentration of the dicarboxylic acid mixture in the purified aqueous dicarboxylic acid mixture solution was 35% by weight, and that the dicarboxylic acid mixture was comprised of 20% by weight of succinic acid, 50% by weight of glutaric acid and 30% by weight of adipic acid. Further, with respect to the dicarboxylic acid mixture, the nitric acid content was 0.03% by weight; the copper content, the vanadium content and the sulfur content were 4 ppm, 4 ppm and 1 ppm, respectively; the absorption coefficient was 0.014 as measured at 355 nm; and the content of an impurity component having an oxygen-nitrogen bond was 1,083 ppm.

Production of a Diol Mixture by a Hydrogenation Reaction

Using the purified aqueous dicarboxylic acid mixture solution obtained above, a diol mixture was produced as follows. 16.1 g of the purified aqueous dicarboxylic acid mixture solution and 0.3 g of the Ru—Sn—Re catalyst prepared in Reference Example 1 were charged into a 100 ml autoclave made of Hastelloy, which was equipped with a magnetic induction type stirrer. The atmosphere in the autoclave was replaced by nitrogen at room temperature and, then, pressurized hydrogen gas was introduced into the autoclave to increase the internal pressure thereof to 2 MPa, and the internal temperature of the autoclave was elevated to 180° C. After the internal temperature of the autoclave reached 180° C., pressurized hydrogen gas was further introduced into the autoclave to increase the internal pressure thereof to 15 MPa and, then, a hydrogenation reaction was performed under the above-mentioned internal pressure for 18 hours. After completion of the hydrogenation reaction, a hydrogenation reaction mixture containing a diol mixture was taken out from the autoclave, while leaving the catalyst in the autoclave. The diol mixture contained in the hydrogenation reaction mixture was analyzed by gas chromatography under the above-mentioned analysis conditions.

Into the autoclave containing the catalyst therein was charged 16.1 g of the purified aqueous dicarboxylic acid mixture solution, and a hydrogenation reaction was performed under substantially the same conditions as mentioned above to produce a diol mixture. This procedure for the hydrogenation of the dicarboxylic acid mixture was repeated 9 times (i.e., 10 runs of the hydrogenation were performed). With respect to the catalyst used, the activity maintenance ratio (%) was calculated by the formula: {(total amount of 1,4-butanediol, 1,5-pentanediol and 1,6-hexanediol which were obtained in the 10th run of the hydrogenation)/(total amount of 1,4-butanediol, 1,5-pentanediol and 1,6-hexanediol which were obtained in the 1st run of the hydrogenation)}×100. The results are shown in Table 2.

EXAMPLE 5

Production of a Diol Mixture by a Hydrogenation Reaction 16.1 g of the purified aqueous dicarboxylic acid mixture solution prepared in Example 4 and 0.3 g of the Ru—Sn—Pt catalyst prepared in Reference Example 2 were charged into a 100 ml autoclave made of Hastelloy, which was equipped with a magnetic induction type stirrer. The atmosphere in the autoclave was replaced by nitrogen at room temperature and, then, pressurized hydrogen gas was introduced into the autoclave to increase the internal pressure thereof to 2 MPa, and the internal temperature of the autoclave was elevated to 180° C. After the internal temperature of the autoclave reached 180° C., pressurized hydrogen gas was further introduced into the autoclave to increase the internal pressure thereof to 15 MPa, and a hydrogenation reaction was performed under the above-mentioned internal pressure for 18 hours. After completion of the hydrogenation reaction, a hydrogenation reaction mixture containing a diol mixture was taken out from the autoclave, while leaving the catalyst in the autoclave. The diol mixture contained in the hydrogenation reaction mixture was analyzed by gas chromatography under the above-mentioned analysis conditions.

Into the autoclave containing the catalyst therein was charged 16.1 g of the purified aqueous dicarboxylic acid mixture solution, and a hydrogenation reaction was performed under substantially the same conditions as mentioned above to produce a diol mixture. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 2.

EXAMPLE 6

Preparation of a Dicarboxylic Acid Mixture
(Preparation by the First Purification Process)

Using the same aqueous by-product solution as used in Example 4, a dicarboxylic acid mixture in the form of a purified aqueous solution thereof was prepared as follows.

1,000 g of the aqueous by-product solution was charged into a beaker and heated at about 120° C. under atmospheric pressure for 1 hour while stirring and, then, at a temperature of from 170 to 175° C. for 30 minutes while stirring to effect dehydration and denitration of the aqueous by-product solution. The resultant mixture was cooled to thereby obtain 380 g of a dehydrated and denitrated dicarboxylic acid mixture. To the obtained dehydrated and denitrated dicarboxylic acid mixture was added ion-exchanged water to thereby obtain an aqueous denitrated dicarboxylic acid mixture solution having a dicarboxylic acid mixture content of 38% by weight. Then, an insoluble matter was removed from the aqueous denitrated dicarboxylic acid mixture solution by filtration to thereby obtain a filtrate. To the obtained filtrate was added 300 g of a styrene polymer type cation exchange resin having a sulfonic acid group as a cation exchange group (trade name: Amberlite IR-120B) (manufactured and sold by ORGANO CORP., Japan), and the resultant mixture was stirred gently at room temperature for 3 hours to cause the cation exchange resin to react with the copper and vanadium which were used as oxidation catalyst, followed by recovering the cation exchange resin by filtration, to thereby remove copper values and vanadium values from the mixture to obtain a filtrate. To the obtained filtrate was added 100 g of a powdery activated carbon, and the resultant mixture was stirred at room temperature for 3 hours. Then, the activated carbon was removed from the mixture by filtration to thereby obtain a filtrate. To the obtained filtrate was added 300 g of a styrene polymer type anion exchange resin having a quaternary ammonium salt as an anion exchange group (trade name: Amberlite IRA-900) (manufactured and sold by ORGANO CORP., Japan), and the resultant mixture was stirred gently at room temperature for 3 hours to cause the anion exchange resin to react with sulfur values, followed by recovering the anion exchange resin by filtration, to thereby remove the sulfur values from the mixture to obtain a dicarboxylic acid mixture in the form of a purified aqueous solution thereof.

The thus obtained, purified aqueous dicarboxylic acid mixture solution was analyzed by HPLC under the above-mentioned analysis conditions. As a result, it was found that the concentration of the dicarboxylic acid mixture in the purified aqueous dicarboxylic acid mixture solution was 35% by weight, and that the dicarboxylic acid mixture was comprised of 20% by weight of succinic acid, 50% by weight of glutaric acid and 30% by weight of adipic acid. Further, with respect to the dicarboxylic acid mixture, the nitric acid content was 0.03% by weight; the copper content, the vanadium content and the sulfur content were 4 ppm, 4 ppm and 1 ppm, respectively: the absorption coefficient was 0.010 as measured at 355 nm; and the content of an impurity component having an oxygen-nitrogen bond was 653 ppm.

Production of a Diol Mixture by a Hydrogenation Reaction

A hydrogenation reaction for producing a diol mixture was performed in substantially the same manner as in Example 1, except that 16.1 g of the purified aqueous dicarboxylic acid mixture solution obtained above was used instead of the water and the dicarboxylic acid mixture prepared in Example 1. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 2.

EXAMPLE 7

Preparation of a Dicarboxylic Acid Mixture
(Preparation by the Second Purification Process)

Using the same aqueous by-product solution as used in Example 4, a dicarboxylic acid mixture was prepared as follows.

1,000 g of the aqueous by-product solution was charged into a beaker and heated at about 120° C. under atmospheric pressure for 1 hour while stirring and, then, at a temperature of from 170 to 175° C. for 30 minutes while stirring to effect dehydration and denitration of the aqueous by-product solution. The resultant mixture was cooled to thereby obtain 380 g of a dehydrated and denitrated dicarboxylic acid mixture. To the obtained dehydrated and denitrated dicarboxylic acid mixture was added ion-exchanged water to thereby obtain an aqueous denitrated dicarboxylic acid mixture solution having a dicarboxylic acid mixture content of 38% by weight. Then, an insoluble matter was removed from the aqueous denitrated dicarboxylic acid mixture solution by filtration to thereby obtain a filtrate. To the obtained filtrate was added 300 g of a styrene polymer type cation exchange resin having a sulfonic acid group as a cation exchange group (trade name: Amberlite IR-120B) (manufactured and sold by ORGANO CORP., Japan), and the resultant mixture was stirred gently at room temperature for 3 hours to cause the cation exchange resin to react with the copper and vanadium which were used as oxidation catalyst, followed by recovering the cation exchange resin by filtration, to thereby remove copper values and vanadium values from the mixture to obtain a filtrate. The obtained filtrate was heated at about 120° C. under atmospheric pressure for 1 hour while stirring to distill off water, followed by cooling, to obtain a denitrated dicarboxylic acid mixture. To the obtained denitrated dicarboxylic acid mixture was added 3,000 g of xylene to thereby obtain a suspension containing dicarboxylic acids. The obtained suspension was heated at about 80° C. for 20 minutes while vigorously stirring, followed by cooling while stirring. The resultant mixture was subjected to filtration to thereby obtain a denitrated dicarboxylic acid mixture as a filtrate. The obtained denitrated dicarboxylic acid mixture was held at 60° C. in vacuo to remove xylene, thereby recovering 361 g of a dicarboxylic acid mixture.

The recovered dicarboxylic acid mixture was analyzed by HPLC under the above-mentioned analysis conditions. As a result, it was found that the dicarboxylic acid mixture was comprised of 20% by weight of succinic acid, 50% by weight of glutaric acid and 30% by weight of adipic acid. Further, with respect to the dicarboxylic acid mixture, the nitric acid content was 0.02% by weight; the copper content, the vanadium content and the sulfur content were 4 ppm, 4 ppm and 10 ppm, respectively; the absorption coefficient was 0.040 as measured at 355 nm; and the content of an impurity component having an oxygen-nitrogen bond was 848 ppm.

Production of a Diol Mixture by a Hydrogenation Reaction

A hydrogenation reaction for producing a diol mixture was performed in substantially the same manner as in Example 1, except that 5.85 g of the dicarboxylic acid mixture recovered above and 10.86 g of ion-exchanged water were used instead of the water and the dicarboxylic acid mixture prepared in Example 1. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 2.

EXAMPLE 8

Preparation of a Dicarboxylic Acid Mixture
(Preparation by the First Purification Process)

Using the same aqueous by-product solution as used in Example 4, a dicarboxylic acid mixture was prepared in the form of a purified aqueous solution thereof as follows.

1,000 g of the aqueous by-product solution was charged into a beaker and heated at about 120° C. under atmospheric pressure for 1 hour while stirring and, then, at a temperature of from 170 to 175° C. for 30 minutes while stirring to effect dehydration and denitration of the aqueous by-product solution. The resultant solution was cooled to thereby obtain 380 g of a dehydrated and denitrated dicarboxylic acid mixture. To the obtained dehydrated and denitrated dicarboxylic acid mixture was added ion-exchanged water to thereby obtain an aqueous denitrated dicarboxylic acid mixture solution having a dicarboxylic acid mixture content of 38% by weight. Then, an insoluble matter was removed from the aqueous denitrated dicarboxylic acid mixture solution by filtration to thereby obtain a filtrate. To the obtained filtrate was added 500 g of a styrene polymer type cation exchange resin having a sulfonic acid group as a cation exchange group (trade name: Amberlite IR-120B) (manufactured and sold by ORGANO CORP., Japan), and the resultant mixture was stirred gently at 80° C. for 3 hours to cause the cation exchange resin to react with the copper and vanadium which were used as oxidation catalyst, followed by recovering the cation exchange resin by filtration, to thereby remove copper values and vanadium values from the mixture to obtain a dicarboxylic acid mixture in the form of a purified aqueous solution.

The thus obtained, purified aqueous dicarboxylic acid mixture solution was analyzed by HPLC under the above-mentioned analysis conditions. As a result, it was found that the concentration of the dicarboxylic acid mixture in the purified aqueous dicarboxylic acid mixture solution was 35% by weight, and that the dicarboxylic acid mixture was comprised of 20% by weight of succinic acid, 50% by weight of glutaric acid and 30% by weight of adipic acid. Further, with respect to the dicarboxylic acid mixture, the nitric acid content was 0.03% by weight; the copper content, the vanadium content and the sulfur content were 3 ppm, 1 ppm and 182 ppm, respectively; the absorption coefficient was 1.437 as measured at 355 nm; and the content of an impurity component having an oxygen-nitrogen bond was 5,600 ppm.

Production of a Diol Mixture by a Hydrogenation Reaction

A hydrogenation reaction for producing a diol mixture was performed in substantially the same manner as in Example 1, except that 16.1 g of the purified aqueous dicarboxylic acid mixture solution obtained above was used instead of the water and the dicarboxylic acid mixture prepared in Example 1. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 2.

TABLE 2

| | Activity maintenance ratio (%) |
|---|---|
| Example 4 | 98 |
| Example 5 | 99 |
| Example 6 | 99 |
| Example 7 | 96 |
| Example 8 | 83 |

EXAMPLE 9

Production of a Diol Mixture by a Hydrogenation Reaction

Using the dicarboxylic acid mixture prepared in Example 1, a diol mixture was produced as follows.

175 g of the dicarboxylic acid mixture prepared in Example 1, 325 g of ion-exchanged water and 10 g of the Ru—Sn—Re catalyst prepared in Reference Example 1 were charged into a 1,000 ml autoclave made of Hastelloy, which was equipped with a magnetic induction type stirrer. The atmosphere in the autoclave was replaced by nitrogen at room temperature and, then, pressurized hydrogen gas was introduced into the autoclave to increase the internal pressure thereof to 2 MPa, and the internal temperature of the autoclave was elevated to 180° C. After the internal temperature of the autoclave reached 180° C., pressurized hydrogen gas was further introduced into the autoclave to increase the internal pressure thereof to 15 MPa and, then, a hydrogenation reaction was performed under the above-mentioned internal pressure for 30 hours. After completion of the hydrogenation reaction, a hydrogenation reaction mixture containing a diol mixture was taken out from the autoclave, while leaving the catalyst in the autoclave. The diol mixture contained in the hydrogenation reaction mixture was analyzed by gas chromatography under the above-mentioned analysis conditions to determine the yields of the diols. As a result, it was found that the yields of 1,4-butanediol, 1,5-pentanediol and 1,6-hexanediol were 89%, 97% and 87%, respectively.

Into the autoclave containing the catalyst therein were charged 175 g of the dicarboxylic acid mixture and 325 g of water, and a hydrogenation reaction was performed under substantially the same conditions as mentioned above to produce a diol mixture. This procedure for the hydrogenation of the dicarboxylic acid mixture was repeated 9 times (i.e., 10 runs of the hydrogenation were performed). In each of the 2nd run through the 10th run of the hydrogenation, the diol mixture contained in the hydrogenation reaction mixture was analyzed by gas chromatography under the above-mentioned analysis conditions to determine the yields of the diols. As a result, it was found that the yields of the diols in each of the 2nd run through the 10th run were approximately the same as those in the 1st run. Further, the hydrogenation reaction mixture was analyzed by HPLC under the above-mentioned analysis conditions. As a result, it was found that the contents of δ-valerolactone and ε-caprolactone in the hydrogenation reaction mixture were each 0.01% or less.

Recovery of 1,4-Butanediol and a Mixture of 1,5-Pentanediol and 1,6-Hexanediol

In the above-mentioned production of the diol mixture, after completion of the hydrogenation reaction, the temperature of the autoclave was lowered to room temperature, and the pressure of the autoclave was reduced to atmospheric pressure to conduct a gas-liquid separation, thereby removing hydrogen gas from the hydrogenation reaction mixture. Approximately 5 kg of the resultant hydrogen gas-removed hydrogenation reaction mixture was heated to 109° C. under atmospheric pressure to distill off about 85% of water contained in the mixture, and a mixture of tetrahydrofuran, tetrahydropyran, butanol and pentanol which had been by-produced in the above-mentioned hydrogenation reaction. The resultant mixture was subjected to distillation using a multi-stage distillation column having 12 stages under conditions wherein the column bottom temperature was 160° C., the column bottom pressure was 6 kPa, the column top temperature was 25° C. and the column top pressure was 3.5 kPa. By the distillation, water and a mixture of γ-butyrolactone, pentanol and hexanol were distilled off, wherein the mixture had been by-produced in the above-mentioned hydrogenation reaction, thereby obtaining a purified diol mixture.

The purified diol mixture obtained was subjected to further distillation using a multi-stage distillation column having 35 stages under conditions wherein the column bottom temperature was 180° C., the column bottom pressure was 12 kPa, the column top temperature was 95° C. and the column top pressure was 3 kPa. By the distillation, 1,4-butanediol was recovered as a low boiling point component. The amount of the recovered 1,4-butanediol was 238 g. The recovered 1,4-butanediol was analyzed by gas chromatography under the above-mentioned analysis conditions. As a result, it was found that the recovered 1,4-butanediol had a purity of 98.5% and contained 1,5-pentanediol as an impurity. It was also found that lactones were not contained in the recovered 1,4-butanediol.

A high boiling point mixture remaining in the column after the recovery of 1,4-butanediol was withdrawn from the bottom of the column and subjected to distillation using a multi-stage distillation column having 7 stages under conditions wherein the column bottom temperature was 200° C., the column bottom pressure was 7 kPa, the column top temperature was 163° C. and the column top pressure was 6 kPa. By the distillation, a mixture of 1,5-pentanediol and 1,6-hexanediol was recovered as a distillate. The amount of the recovered mixture was 866 g. The recovered mixture of 1,5-pentanediol and 1,6-hexanediol was analyzed by gas chromatography under the above-mentioned analysis conditions. As a result, it was found that the recovered mixture had a purity of 99.8% and contained 1,4-butanediol as an impurity. It was also found that 1,5-hexanediol and 1,4-dihydroxycyclohexane were not contained in the mixture.

EXAMPLE 10

Preparation of a Dicarboxylic Acid Mixture
(Preparation by the Third Purification Process)

A dicarboxylic acid mixture was prepared by using an aqueous by-product solution obtained in an adipic acid production process, from which adipic acid had been isolated, and from which nitric acid and the catalyst used had been removed. The aqueous by-product solution was comprised of 19% by weight of glutaric acid, 6% by weight of succinic acid and 5% by weight of adipic acid. Further, with respect to the aqueous by-product solution, the nitric acid content was 4.1% by weight; the copper content, the vanadium content and the sulfur content were 7 ppm, 5 ppm and 230 ppm, respectively; the content of an impurity component having an oxygen-nitrogen bond was 6,640 ppm; the remainder of the solution (i.e., component other than mentioned above) was water; and the absorption coefficient was 0.79 as measured at 355 nm.

The aqueous by-product solution was subjected to reduction treatment as follows. 15.0 g of the aqueous by-product solution and 0.15 g of a platinum catalyst (comprising an activated carbon having carried thereon 3% by weight of platinum) (manufactured and sold by N. E. CHEMCAT CORPORATION, Japan) were charged into a 100 ml autoclave made of Hastelloy, which was equipped with a magnetic induction type stirrer. The atmosphere in the autoclave was replaced by nitrogen and, then, replaced by hydrogen at room temperature. Then, pressurized hydrogen gas was introduced into the autoclave to increase the internal pressure thereof to 1 MPa, and the internal temperature of the autoclave was elevated to 140° C. After the internal temperature of the autoclave reached 140° C., pressurized hydrogen gas was further introduced into the autoclave to increase the internal pressure thereof to 1.5 MPa. The reduction of nitric acid and an impurity component having an oxygen-nitrogen bond contained in the aqueous by-product solution was performed under the above-mentioned internal pressure for 4 hours. After completion of the reduction treatment, the catalyst was separated from the resultant mixture to thereby obtain a dicarboxylic acid mixture in the form of an aqueous solution thereof.

The obtained dicarboxylic acid mixture was comprised of 19% by weight of glutaric acid, 6% by weight of succinic acid and 5% by weight of adipic acid. Further, with respect to the dicarboxylic acid mixture, the nitric acid content was 0.036% by weight; the copper content, the vanadium content and the sulfur content were 7 ppm, 5 ppm and 170 ppm, respectively; and the absorption coefficient was 0.043 as measured at 355 nm.

Production of a Diol Mixture by a Hydrogenation Reaction

A hydrogenation reaction was performed in substantially the same manner as in Example 1, except that 15.0 g of the aqueous dicarboxylic acid mixture solution obtained above was used instead of the water and the dicarboxylic acid mixture prepared in Example 1. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 3.

EXAMPLE 11

Preparation of a Dicarboxylic Acid Mixture
(Preparation by the Third Purification Process)

Using the same aqueous by-product solution as used in Example 10, a dicarboxylic acid mixture was prepared as follows.

To 500 g of the aqueous by-product solution was added 120 g of a styrene polymer type cation exchange resin having a sulfonic acid group as a cation exchange group (trade name: Amberlite IR-120B) (manufactured and sold by ORGANO CORP., Japan), and the resultant mixture was stirred gently at room temperature for 3 hours to cause the cation exchange resin to react with the copper and vanadium which were used as oxidation catalyst, followed by recovering the cation exchange resin by filtration, to thereby remove copper values and vanadium values from the mixture. The resultant aqueous by-product solution was subjected to substantially the same reduction treatment as in Example 10. After completion of the reduction treatment, the catalyst was separated from the resultant mixture to thereby obtain an dicarboxylic acid mixture in the form of an aqueous solution thereof.

The obtained dicarboxylic acid mixture was comprised of 19% by weight of glutaric acid, 6% by weight of succinic acid and 5% by weight of adipic acid. Further, with respect to the dicarboxylic acid mixture, the nitric acid content was 0.031% by weight; the copper content, the vanadium content and the sulfur content were 3 ppm, 3 ppm and 180 ppm, respectively; and the absorption coefficient was 0.040 as measured at 355 nm.

Production of a Diol Mixture by a Hydrogenation Reaction

A hydrogenation reaction for producing a diol mixture was performed in substantially the same manner as in Example 1, except that 15.0 g of the aqueous dicarboxylic acid mixture solution obtained above was used instead of the water and the dicarboxylic acid mixture prepared in Example 1. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 3.

EXAMPLE 12

Preparation of a Dicarboxylic Acid Mixture
(Preparation by the Third Purification Process)

Using the same aqueous by-product solution as used in Example 10, a dicarboxylic acid mixture was prepared as follows.

The aqueous by-product solution was subjected to substantially the same reduction treatment as in Example 10, except that the reduction treatment was performed at 60° C. under a pressure of 2.0 MPa for 6 hours. After completion of the reduction treatment, the catalyst was separated from the resultant mixture to thereby obtain a dicarboxylic acid mixture in the form of an aqueous solution thereof.

The obtained dicarboxylic acid mixture was comprised of 19% by weight of glutaric acid, 6% by weight of succinic acid and 5% by weight of adipic acid. Further, with respect to the dicarboxylic acid mixture, the nitric acid content was 0.18% by weight; the copper content, the vanadium content and the sulfur content were 7 ppm, 5 ppm and 160 ppm, respectively; and the absorption coefficient was 0.061 as measured at 355 nm.

Production of a Diol Mixture by a Hydrogenation Reaction

A hydrogenation reaction for producing a diol mixture was performed in substantially the same manner as in Example 1, except that 15.0 g of the aqueous dicarboxylic acid mixture solution obtained above was used instead of the water and the dicarboxylic acid mixture prepared in Example 1. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 3.

EXAMPLE 13

Preparation of a Dicarboxylic Acid Mixture
(Preparation by the Third Purification Process)

Using the same aqueous by-product solution as used in Example 10, a dicarboxylic acid mixture was prepared as follows.

To 500 g of the aqueous by-product solution was added 120 g of a styrene polymer type cation exchange resin having a sulfonic acid group as a cation exchange group (trade name: Amberlite IR-120B) (manufactured and sold by ORGANO CORP., Japan), and the resultant mixture was stirred gently at room temperature for 3 hours to cause the cation exchange resin to react with the copper and vanadium which were used as oxidation catalyst, followed by recovering the cation exchange resin by filtration, to thereby remove copper values and vanadium values from the mixture. The resultant aqueous by-product solution was subjected to substantially the same reduction treatment as in Example 10, except that, as a catalyst, a ruthenium catalyst (comprising an activated carbon having carried thereon 5.0% by weight of ruthenium) (manufactured and sold by N. E. CHEMCAT CORPORATION, Japan) was used. After completion of the reduction treatment, the catalyst was separated from the resultant mixture to thereby obtain a dicarboxylic acid mixture in the form of an aqueous solution thereof.

The obtained dicarboxylic acid mixture was comprised of 19% by weight of glutaric acid, 6% by weight of succinic acid and 5% by weight of adipic acid. Further, with respect to the dicarboxylic acid mixture, the nitric acid content was 0.073% by weight; the copper content, the vanadium content and the sulfur content were 5 ppm, 5 ppm and 190 ppm, respectively; and the absorption coefficient was 0.038 as measured at 355 nm.

Production of a Diol Mixture by a Hydrogenation Reaction

A hydrogenation reaction for producing a diol mixture was performed in substantially the same manner as in Example 1, except that 15.0 g of the aqueous dicarboxylic acid mixture solution obtained above was used instead of the water and the dicarboxylic acid mixture prepared in Example 1. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 3.

EXAMPLE 14

Preparation of a Dicarboxylic Acid Mixture
(Preparation by the Third Purification Process)

A dicarboxylic acid mixture was prepared by using the same aqueous by-product solution as used in Example 10. As mentioned above, the aqueous by-product solution was comprised of 19% by weight of glutaric acid, 6% by weight of succinic acid and 5% by weight of adipic acid. Further, with respect to the aqueous by-product solution, the nitric acid content was 4.1% by weight; the absorption coefficient was 0.79 as measured at 355 nm; and the content of an impurity component having an oxygen-nitrogen bond was 6,640 ppm.

1,000 g of the aqueous by-product solution was charged into a beaker and heated at about 120° C. under atmospheric pressure for 1 hour while stirring and, then, at a temperature of from 170 to 175° C. under atmospheric pressure for 30 minutes while stirring to effect dehydration and denitration of the aqueous by-product solution. The resultant mixture was cooled to thereby obtain 300 g of a dehydrated and denitrated dicarboxylic acid mixture. To the obtained dehydrated and denitrated dicarboxylic acid mixture was added ion-exchanged water to thereby obtain an aqueous denitrated dicarboxylic acid mixture solution having a dicarboxylic acid mixture content of 30% by weight. 15.0 g of the obtained aqueous denitrated dicarboxylic acid mixture solution and 0.15 g of the ruthenium catalyst used in Example 13 were charged into a 100 ml autoclave made of Hastelloy, which was equipped with a magnetic induction type stirrer. The atmosphere in the autoclave was replaced by nitrogen and, then, replaced by hydrogen at room temperature. Then, pressurized hydrogen gas was introduced into the autoclave to increase the internal pressure thereof to 1 MPa at room temperature and, then, the internal temperature of the autoclave was elevated to 140° C. After the internal temperature of the autoclave reached 140° C., pressurized hydrogen gas was further introduced into the autoclave to increase the internal pressure thereof to 1.5 MPa. The reduction of nitric acid and an impurity component having an oxygen-nitrogen bond contained in the aqueous denitrated dicarboxylic acid mixture solution was performed under the above-mentioned internal pressure for 4 hours. After completion of the reduction, the catalyst was separated from the resultant mixture to thereby obtain a dicarboxylic acid mixture in the form of an aqueous solution thereof.

The obtained dicarboxylic acid mixture was comprised of 19% by weight of glutaric acid, 6% by weight of succinic acid and 5% by weight of adipic acid. Further, with respect to the dicarboxylic acid mixture, the nitric acid content was 0.005% by weight; the copper content, the vanadium content and the sulfur content were 7 ppm, 5 ppm and 160 ppm, respectively; and the absorption coefficient was 0.021 as measured at 355 nm.

Production of a Diol Mixture by a Hydrogenation Reaction

A hydrogenation reaction for producing a diol mixture was performed in substantially the same manner as in Example 1, except that 15.0 g of the aqueous dicarboxylic acid mixture solution obtained above was used instead of the water and the dicarboxylic acid mixture prepared in Example 1. This procedure for the hydrogenation of the dicarboxylic acid mixture was repeated 9 times (i.e., 10 runs of the hydrogenation were performed). With respect to the catalyst used, the activity maintenance ratio (%) was calculated by the formula described in Example 4. The results are shown in Table 3.

TABLE 3

|  | Activity maintenance ratio (%) |
| --- | --- |
| Example 10 | 98 |
| Example 11 | 95 |
| Example 12 | 89 |
| Example 13 | 92 |
| Example 14 | 96 |

INDUSTRIAL APPLICABILITY

The method of the present invention for producing a diol mixture is advantageous not only in that an aqueous by-product solution (containing a dicarboxylic acid mixture comprising succinic acid, glutaric acid and adipic acid) obtained in an adipic acid production process, which has little utility except for the use as a solvent, can be used as a raw material for a useful diol mixture, but also in that a diol mixture comprising 1,4-butanediol, 1,5-pentanediol and 1,6-hexanediol can be produced stably for a long period of time directly from dicarboxylic acids by hydrogenation thereof, not through esterification thereof. The diols produced by the method of the present invention are useful as raw materials for polyurethanes and polyesters.

What is claimed is:

1. A method for producing a diol mixture comprising 1,4-butanediol, 1,5-pentanediol and 1,6-hexanediol, which comprises:

(A) providing a dicarboxylic acid mixture comprising succinic acid, glutaric acid and adipic acid and having a nitric acid content of 0.2% by weight or less, based on the total weight of said succinic, glutaric and adipic acids, said dicarboxylic acid mixture being prepared by denitrating an aqueous by-product solution obtained in an adipic acid production process comprising subjecting at least one $C_6$ cyclic aliphatic compound to oxidation with nitric acid in an aqueous medium in the presence of an oxidation catalyst to thereby obtain an aqueous reaction mixture comprising succinic acid, glutaric acid and adipic acid, depositing crystals of the adipic acid, and isolating the deposited crystals from said reaction mixture to obtain the aqueous by-product solution; and (B) subjecting said dicarboxylic acid mixture to hydrogenation in the presence of water, hydrogen gas and a hydrogenation catalyst containing an active metal species comprising ruthenium and tin, to thereby obtain a hydrogenation reaction mixture comprising a diol mixture comprising 1,4-butanediol, 1,5-pentanediol and 1,6-hexanediol.

2. The method according to claim 1, wherein, before step (B), said dicarboxylic acid mixture is adjusted to satisfy at least one condition selected from the group consisting of the following conditions (1) and (2):

(1) the mixture has a copper content of 10 ppm by weight or less and a vanadium content of 10 ppm by weight or less, each based on the total weight of said succinic, glutaric and adipic acids; and (2) the mixture has a sulfur content of 200 ppm by weight or less, based on the total weight of said succinic, glutaric and adipic acids.

3. The method according to claim 2, wherein, in said condition (2), the mixture has a sulfur content of 40 ppm by weight or less, based on the total weight of said succinic, glutaric and adipic acids.

4. The method according to claim 1, wherein said dicarboxylic acid mixture in the form of a solution thereof in distilled water exhibits an absorption coefficient of 0.3 or less as measured at 355 nm, wherein said absorption coefficient is determined by the following formula:

$$E=A/(c\times b)$$

wherein E represents the absorption coefficient as measured at 355 nm,

A represents the absorbance of the solution of the dicarboxylic acid mixture in distilled water at room temperature, c represents the amount (g) of the dicarboxylic acid mixture dissolved in 100 g of distilled water, and b represents the length (cm) of a cell used for measuring the absorbance.

5. The method according to claim 4, wherein said dicarboxylic acid mixture in the form of a solution thereof in distilled water exhibits an absorption coefficient of 0.1 or less.

6. The method according to claim 1 or 2, wherein said dicarboxylic acid mixture contains an impurity component having an oxygen-nitrogen bond in an amount of 2,000 ppm by weight or less in terms of the amount of nitric acid, based on the total weight of said succinic, glutaric and adipic acids.

7. The method according to claim 1, wherein said active metal species contained in said hydrogenation catalyst further comprises at least one metal selected from the group consisting of metals of Group 7 of the Periodic Table.

8. The method according to claim 7, wherein said at least one metal selected from the group consisting of metals of Group 7 of the Periodic Table is rhenium.

9. The method according to claim 1 or 7, wherein said active metal species contained in said hydrogenation catalyst further comprises at least one metal selected from the group consisting of metals of Group 8 of the Periodic Table other than ruthenium and metals of Groups 9 and 10 of the Periodic Table.

10. The method according to claim 9, wherein said at least one metal selected from the group consisting of metals of Group 8 of the Periodic Table other than ruthenium and metals of Groups 9 and 10 of the Periodic Table, is platinum.

11. The method according to claim 1, wherein said hydrogenation catalyst further comprises an activated carbon having carried thereon said active metal species.

12. The method according to claim 1, wherein said hydrogenation is conducted under conditions wherein the temperature is from 100 to 300° C. and the hydrogen pressure is from 1 to 25 MPa.

13. The method according to claim 1, wherein said dicarboxylic acid mixture is prepared in the form of an aqueous solution thereof by a first purification process comprising the steps of:
(a) heating said aqueous by-product solution at a temperature of from 80 to 200° C. under atmospheric or lower pressure to effect dehydration and denitration of said aqueous by-product solution to obtain a dehydrated and denitrated dicarboxylic acid mixture;
(b) adding water to the obtained dehydrated and denitrated dicarboxylic acid mixture to thereby obtain an aqueous denitrated dicarboxylic acid mixture solution; and
(c) contacting said aqueous denitrated dicarboxylic acid mixture solution with a cation exchange resin to thereby remove copper values and vanadium values.

14. The method according to claim 13, wherein said first purification process further comprises step (d) of contacting said aqueous denitrated dicarboxylic acid mixture solution with an anion adsorptive substance.

15. The method according to claim 13 or 14, wherein said first purification process further comprises the step of contacting said aqueous denitrated dicarboxylic acid mixture solution with an activated carbon.

16. The method according to claim 1, wherein said dicarboxylic acid mixture is prepared by a second purification process comprising the steps of:
(a) heating said aqueous by-product solution at a temperature of from 80 to 130° C. under atmospheric or lower pressure, followed by heating at a temperature of from higher than 130° C. to 180° C. under atmospheric pressure, to thereby obtain a dehydrated and denitrated dicarboxylic acid mixture;
(b) adding water to the obtained dehydrated and denitrated dicarboxylic acid mixture to thereby obtain an aqueous denitrated dicarboxylic acid mixture solution;
(c) contacting said aqueous denitrated dicarboxylic acid mixture solution with a cation exchange resin to thereby remove copper values and vanadium values;
(d) heating the resultant aqueous denitrated dicarboxylic acid mixture solution under atmospheric or lower pressure at a temperature sufficient to distill off water from said resultant aqueous denitrated dicarboxylic acid mixture solution and obtain a denitrated dicarboxylic acid mixture;
(e) adding a $C_6$–$C_{14}$ aromatic hydrocarbon having a boiling point of 200° C. or less under atmospheric pressure to the denitrated dicarboxylic acid mixture obtained in step (d), and heating the resultant mixture at a temperature which is not higher than the boiling point of said aromatic hydrocarbon, followed by cooling; and
(f) recovering the denitrated dicarboxylic acid mixture from said mixture by filtration, thereby preparing said dicarboxylic acid mixture.

17. The method according to claim 16, wherein said second purification process further comprises, after step (a), the step of contacting the aqueous denitrated dicarboxylic acid mixture solution or an aqueous solution of the denitrated dicarboxylic acid mixture in water, with an anion adsorptive substance.

18. The method according to claim 1, wherein said dicarboxylic acid mixture is prepared in the form of an aqueous solution thereof by a third purification process comprising:
contacting said aqueous by-product solution with hydrogen gas in the presence of a reduction catalyst containing an active metal species comprising at least one metal selected from the group consisting of metals of Groups 7 to 10 of the Periodic Table, to thereby reduce nitric acid and an impurity component having an oxygen-nitrogen bond contained in said aqueous by-product solution, thereby obtaining said dicarboxylic acid mixture in the form of an aqueous solution thereof.

19. The method according to claim 18, wherein said reduction of the nitric acid and an impurity component having an oxygen-nitrogen bond in said third purification process is conducted under conditions wherein the temperature is from 50 to 200° C. and the hydrogen pressure is from 0.2 to 5 MPa.

20. The method according to claim 18 or 19, wherein said active metal species contained in said reduction catalyst used in said third purification process is at least one metal selected from the group consisting of platinum, rhenium, palladium, rhodium, nickel, iridium and ruthenium.

21. The method according to claim 18, wherein, prior to the contacting of said aqueous by-product solution with hydrogen gas in said third purification process, said aqueous by-product solution is heated at a temperature of from 80 to 130° C. under atmospheric or lower pressure and then heated at a temperature of from higher than 130° C. to 180° C. under atmospheric pressure, followed by addition of water thereto.

22. A method for recovering 1,4-butanediol and a mixture of 1,5-pentanediol and 1,6-hexanediol from the diol mixture obtained by the method of claim 1, which comprises:
(i) adjusting the temperature of said hydrogenation reaction mixture comprising the diol mixture to a temperature of from room temperature to less than 100° C., followed by a gas-liquid separation under atmospheric or lower pressure under which water is not boiled at the adjusted temperature of the mixture to remove the hydrogen gas from the hydrogenation reaction mixture to remove the hydrogen gas from said hydrogenation reaction mixture;

(ii) heating the hydrogen gas-removed hydrogenation reaction mixture under atmospheric pressure to thereby distill off the water and a mixture of cyclic ethers and monohydric alcohols which is by-produced in said hydrogenation reaction;

(iii) subjecting the resultant mixture to multi-stage distillation to distill off the water and γ-butyrolactone by-produced in the hydrogenation reaction, thereby obtaining a purified diol mixture;

(iv) subjecting the purified diol mixture to multi-stage distillation to obtain 1,4-butanediol as a low boiling point component while withdrawing a high boiling point mixture; and (v) subjecting the high boiling point mixture obtained in step (iv) to multi-stage distillation to obtain a mixture of 1,5-pentanediol and 1,6-hexanediol as a distillate.

* * * * *